United States Patent
Kang et al.

(10) Patent No.: US 12,040,087 B2
(45) Date of Patent: Jul. 16, 2024

(54) METHOD OF CONTROLLING USER EQUIPMENT FOR MEDICAL CHECK-UP AND APPARATUS FOR PERFORMING THE METHOD

(71) Applicant: WELT CORP., LTD., Seoul (KR)

(72) Inventors: Seong Ji Kang, Seoul (KR); Hye Kang Roh, Seoul (KR); Hye Ryong Kim, Gyeonggi-do (KR); Hwa Young Jeong, Gyeonggi-do (KR)

(73) Assignee: WELT CORP., LTD., Seoul (KR)

( * ) Notice: Subject to any disclaimer, the term of this patent is extended or adjusted under 35 U.S.C. 154(b) by 346 days.

(21) Appl. No.: 17/114,868

(22) Filed: Dec. 8, 2020

(65) Prior Publication Data
US 2022/0165408 A1 May 26, 2022

(30) Foreign Application Priority Data

Nov. 26, 2020 (KR) ........................ 10-2020-0161097

(51) Int. Cl.
*G16H 40/67* (2018.01)
*A61B 5/00* (2006.01)
(Continued)

(52) U.S. Cl.
CPC ........... *G16H 40/67* (2018.01); *A61B 5/0002* (2013.01); *A61B 5/02438* (2013.01);
(Continued)

(58) Field of Classification Search
CPC ........ G16H 40/67; G16H 10/60; G16H 50/20; G16H 20/10; A61B 5/0002;
(Continued)

(56) References Cited

U.S. PATENT DOCUMENTS

2011/0245633 A1* 10/2011 Goldberg ............... A61B 5/165
600/323
2017/0000416 A1* 1/2017 EhrenKranz ....... G08B 21/0453
(Continued)

FOREIGN PATENT DOCUMENTS

CN 107016225 A * 8/2017 ........... A61B 5/0022

OTHER PUBLICATIONS

S. Dudakiya, H. Galani, A. Shaikh, D. Thanki, R. A. Late and S. E. Pawar, "Monitoring mobile patients using predictive analysis by data from wearable sensors," 2016 International Conference on Electrical, Electronics, and Optimization Techniques (ICEEOT), 2016 (Year: 2016).*

(Continued)

*Primary Examiner* — Evangeline Barr
*Assistant Examiner* — Patricia K. Edouard
(74) *Attorney, Agent, or Firm* — Mark T. Vogelbacker; Eckert Seamans Cherin & Mellott, LLC

(57) ABSTRACT

A method of controlling user equipment for a medical checkup and an apparatus for performing the method include controlling user equipment for a medical checkup the includes generating digital biomarker control data by a diagnosis server on the basis of prescription data, and transmitting the digital biomarker control data to user equipment by the diagnosis server, wherein the digital biomarker control data includes information for controlling a digital biomarker module of the user equipment.

14 Claims, 16 Drawing Sheets

(51) Int. Cl.
*A61B 5/024* (2006.01)
*A61B 5/08* (2006.01)
*G16H 10/60* (2018.01)
*G16H 20/10* (2018.01)
*G16H 50/20* (2018.01)
*H04L 67/12* (2022.01)

(52) U.S. Cl.
CPC .......... *A61B 5/0816* (2013.01); *A61B 5/7264* (2013.01); *A61B 5/7267* (2013.01); *G16H 10/60* (2018.01); *G16H 20/10* (2018.01); *G16H 50/20* (2018.01); A61B 5/486 (2013.01); A61B 5/681 (2013.01); A61B 5/6831 (2013.01); A61B 5/6898 (2013.01); A61B 2560/0242 (2013.01); A61B 2562/0219 (2013.01); *H04L 67/12* (2013.01)

(58) Field of Classification Search
CPC . A61B 5/02438; A61B 5/0816; A61B 5/7264; A61B 5/486; A61B 5/681; A61B 5/6831; A61B 5/6898; A61B 2560/0242; H04L 67/12
See application file for complete search history.

(56) References Cited

U.S. PATENT DOCUMENTS

| | | | |
|---|---|---|---|
| 2017/0351819 A1* | 12/2017 | Yamamoto | G06F 16/285 |
| 2018/0137941 A1* | 5/2018 | Chen | G06N 3/04 |
| 2019/0139643 A1* | 5/2019 | Li | G06N 3/045 |
| 2019/0148010 A1* | 5/2019 | Aliamiri | A61B 5/0002 705/2 |
| 2019/0221308 A1* | 7/2019 | Makaron | G16H 50/20 |
| 2020/0113506 A1* | 4/2020 | Liu | A61B 5/0022 |
| 2020/0185107 A1* | 6/2020 | Cox | G16H 50/50 |
| 2020/0356846 A1* | 11/2020 | Saripalli | G06N 3/045 |
| 2020/0387810 A1* | 12/2020 | Hodgson | G06N 20/00 |

OTHER PUBLICATIONS

H. Yin and N. K. Jha, "A Health Decision Support System for Disease Diagnosis Based on Wearable Medical Sensors and Machine Learning Ensembles," in IEEE Transactions on Multi-Scale Computing Systems, vol. 3, No. 4, pp. 228-241, Oct. 1-Dec. 2017, doi: 10.1109/TMSCS.2017.2710194. (Year: 2017).*

* cited by examiner

METHOD OF CONTROLLING USER EQUIPMENT FOR MEDICAL CHECK-UP AND APPARATUS FOR PERFORMING THE METHOD

CROSS-REFERENCE TO RELATED APPLICATIONS

The present application claims priority to and the benefit from Korean Patent Application No. 10-2020-0161097, filed Nov. 26, 2020, which is hereby incorporated by reference in its entirety.

BACKGROUND

1. Field of the Invention

The present disclosure relates to a method of controlling user equipment for a medical checkup and an apparatus for performing the method. More specifically, the present disclosure relates to a method of controlling user equipment for a medical checkup for diagnosing a user's condition on the basis of various types of data collected by a digital biomarker module (e.g., a sensor), and an apparatus for performing the method.

2. Discussion of Related Art

With the development of various smart technologies, data about personal daily activities can be recorded and personal life can be managed more efficiently based on the recorded data. In particular, as interest in health increases, health-related data logging is drawing attention. Many users have already generated and used various types of health-related data about exercise, diet and sleep through user equipment such as smartphones and wearable devices. In the past, health-related data was generated and managed only by medical institutions but users have started to generate and manage their own health-related data by themselves through user equipment such as smartphones and wearable devices.

Health-related data logging is often done through wearable devices. Wearable devices refer to user equipment that users carry or that is attached to users' body. Wearable devices have been widely used to collect health-related data due to the development of the Internet of things and the like. Wearable devices are capable of collecting information regarding a change in users' condition and environments surrounding users and providing advice necessary for the users' health on the basis of the collected data.

Currently, procedures of providing feedback using health-related data obtained through a wearable device are not elaborated and thus are not used in medical practice. However, health-related data obtained through user equipment can be used in actual medical practice owing to the development of not only wearable devices but also user equipment capable of collecting various types of health-related data and the elaboration of decision algorithms based on health-related data obtained through user equipment.

Therefore, it is necessary to develop a sophisticated system for accurately obtaining health-related data through user equipment and using the obtained health-related data in medical practice.

SUMMARY OF THE INVENTION

It is an object of the present disclosure to solve all of the above-described problems.

The present disclosure is directed to obtaining digital biomarker data to effectively diagnose a user's health condition.

The present disclosure is also directed to generating prescription data on the basis of digital biomarker data, and effectively performing user health management by a user through user equipment according to the prescription data.

The present disclosure is also directed to controlling the operation of a digital biomarker module of user equipment according to diagnostic result data and prescription data.

In addition, the present disclosure is directed to providing optimal prescription data according to diagnostic result data through machine-learning-based learning on the basis of a user's diagnostic result data and prescription data.

A representative configuration of the present disclosure for achieving the above objects is as follows.

According to one aspect of the present disclosure, a method of controlling user equipment for a medical checkup includes generating, by a diagnosis server, digital biomarker control data on the basis of prescription data, and transmitting, by the diagnosis server, the digital biomarker control data to user equipment, wherein the digital biomarker control data includes information for controlling a digital biomarker module of the user equipment.

The digital biomarker control data may include at least one of digital biomarker type data, digital biomarker operation data, and digital biomarker collection completion condition data.

The prescription data may be generated on the basis of diagnostic result data input to a machine learning model.

According to another aspect of the present disclosure, a diagnosis server for controlling user equipment for a medical checkup includes a communicator configured to communicate with user equipment, and a processor operatively connected to the communicator, wherein the processor is configured to: generate digital biomarker control data on the basis of prescription data and transmit the digital biomarker control data to the user equipment, and the digital biomarker control data includes information for controlling a digital biomarker module of the user equipment.

The digital biomarker control data may include at least one of digital biomarker type data, digital biomarker operation data, and digital biomarker collection completion condition data.

The prescription data may be generated on the basis of diagnostic result data input to a machine learning model.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
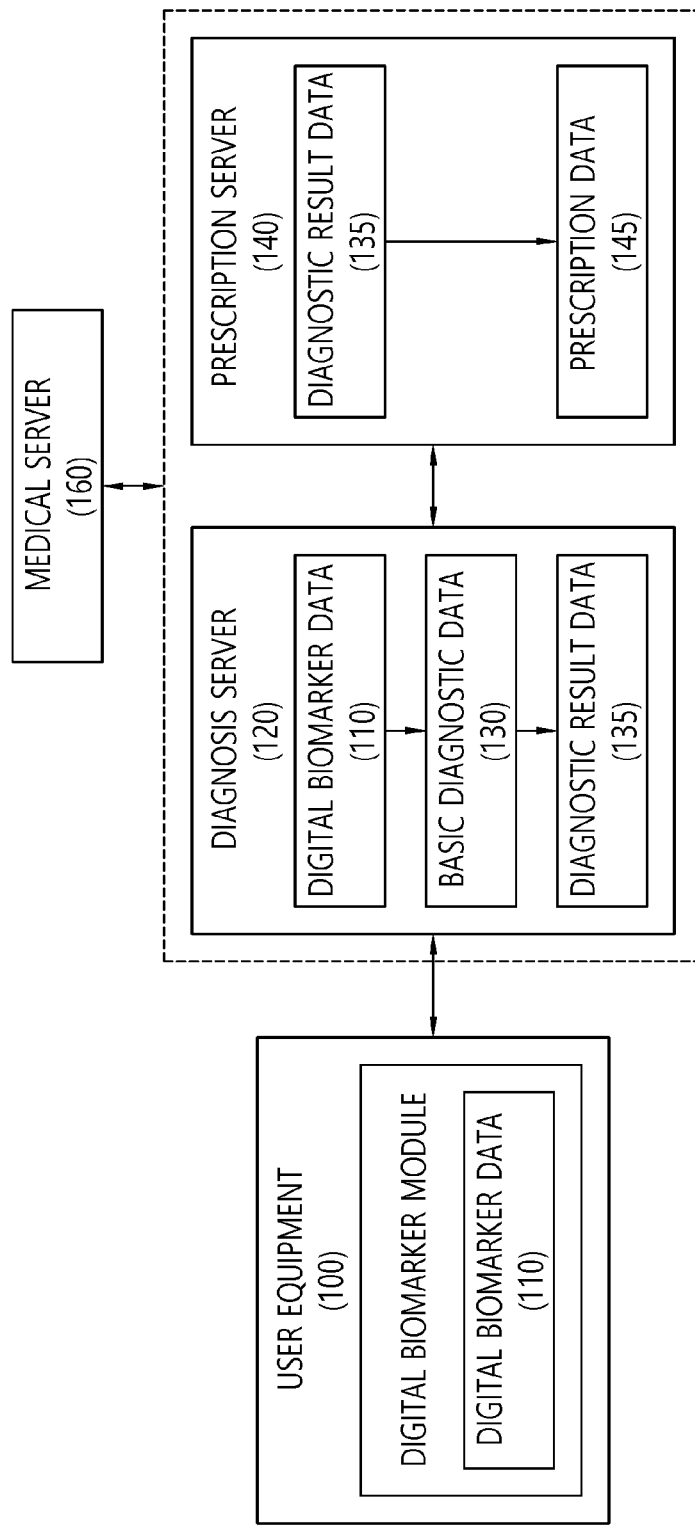
FIG. 1 is a conceptual diagram of a user health diagnosis system based on a digital biomarker according to an embodiment of the present disclosure.

Hereinafter, the present disclosure will be described in detail with respect to embodiments thereof as examples with reference to the accompanying drawings. These embodiments will be described herein in sufficient detail to enable those of ordinary skill in the art to practice the present disclosure. It should be understood that various embodiments of the present disclosure are different from each other but need not be mutually exclusive. For example, specific shapes, structures, and features according to one embodiment described herein may be implemented in a different embodiment by making modifications therein without departing from the spirit and scope of the present disclosure. In addition, it should be understood that the position or arrangement of each element in each embodiment may be changed without departing from the spirit and scope of the present disclosure. Therefore, the following detailed description is not for purpose of limitation, and the scope of the present disclosure should be understood to cover the scope claimed in the claims and all scopes of equivalents thereof. In the drawings, like reference numerals represent the same or similar elements in various aspects.

Hereinafter, various embodiments of the present disclosure will be described in detail with reference to the accompanying drawings so that those of ordinary skill in the art can easily implement the present disclosure.

FIG. 1 is a conceptual diagram of a user health diagnosis system based on a digital biomarker according to an embodiment of the present disclosure.

FIG. 1 illustrates a method of diagnosing a user's health on the basis of digital biomarker data obtained through user equipment.

Referring to FIG. 1, the user health diagnosis system may include user equipment 100, a diagnosis server 120, a prescription server 140, and a medical server 160.

The user equipment 100 may be implemented to obtain digital biomarker data 110.

A digital biomarker is an element available as a marker for diagnosing a user's condition, and may be obtained through a digital biomarker module (e.g., a sensor) implemented in the user equipment 100 or according to a user input. The digital biomarker module may be a device that collects and generates the digital biomarker data 110.

The digital biomarker data 110 may be data related to a digital biomarker.

The digital biomarker may be obtained based on various types of user equipment 100 such as a smart phone, a smart watch, and a smart belt. Digital biomarkers may be classified into a digital biomarker (first type) (or digital biomarker data (first type)), which is directly obtained through the user equipment 100 without additional data input by a user and a digital biomarker (second type) (or digital biomarker data (second type)). For example, a digital biomarker (first type) may be a marker, such as a heart rate or a respiration rate, obtained through the user equipment 100, and a digital biomarker (second type) may be a marker obtained based on a user's direct input, such as response data to a medical questionnaire, provided through the user equipment 100.

At least one user equipment 100 may be registered to correspond to a user identifier of a user so as to obtain the digital biomarker data 110, and the user identifier may be added to the digital biomarker data 110 generated by the at least one user equipment 100 and transmitted to the diagnosis server 120.

The diagnosis server 120 may be implemented to perform a diagnosis on the basis of the digital biomarker data 110 obtained through the user equipment 100. The diagnosis server 120 may generate basic diagnostic data 130 on the basis of the digital biomarker data 110 and generate diagnostic result data 135 on the basis of the generated basic diagnostic data 130.

The basic diagnostic data 130 is data that is a basis of a diagnosis, which is generated based on the digital biomarker data 110, and a piece of the digital biomarker data 110 may be connected with at least one piece of the basic diagnostic data 130. For example, the digital biomarker data 110 may be acceleration data, and the basic diagnostic data 130 connected with the acceleration data, which is the digital biomarker data 110, may include hand tremor, a time taken to fall asleep, sleeping hours, a walking pattern, seizure, etc.

The diagnostic result data 135 may be a result of judging a user's condition on the basis of the basic diagnostic data 130. Specifically, the diagnostic result data 135 may include a result of judging a risk of a certain target disease (e.g., alcoholism, insomnia, sarcopenia, epilepsy, obesity, etc.).

The diagnosis server 120 may generate the basic diagnostic data 130/the diagnostic result data 135 on the basis of digital biomarker data selected from the digital biomarker data 110 obtained through at least one user equipment 100 of the user. For example, digital biomarker data (smart phone), digital biomarker data (smart watch), and digital biomarker data (smart belt) may be transmitted to the diagnosis server 120 from a plurality of types of user equipment such as a smart phone, a smart watch, and a smart belt, which are registered using a user identifier. The diagnosis server 120 may generate the basic diagnostic data 130/the diagnostic result data 135 by selecting only the digital biomarker 110 necessary to generate the basic diagnostic data 130 from among a plurality of pieces of digital biomarker data.

The diagnosis server 120 may generate the basic diagnostic data 130/the diagnostic result data 135 on the basis of a self-diagnosis algorithm but may operate in connection with a medical server. Whether to generate the basic diagnostic data 130/the diagnostic result data 135 on the basis of the diagnosis algorithm of the diagnosis server 120 or in additional consideration of a judgment of a professional medical team in connection with a medical server may be determined according to the set-up.

The medical server 160 may be implemented to support the generation of the basic diagnostic data 130, the diagnostic result data 135, and/or prescription data 145, in conjunction with the diagnosis server 120 and the prescription server 140. For example, the medical server 160 may request the diagnosis server 120 to provide digital biomarker data and provide the diagnosis server 120 with additional basic diagnostic data and/or additional diagnostic result data based on the digital biomarker data so as to support the generation of the basic diagnostic data 130, the diagnostic result data 135, and/or the prescription data 145.

The prescription server 140 may be implemented to generate the prescription data 145 on the basis of the diagnostic result data 135. The prescription data 145 may include information regarding a desired treatment according to the diagnostic result data 135. The prescription data 145 may include various types of data for improving a user's condition, such as prescription data for medicine, behavior correction data for correcting a behavior, recommended exercise data, and the like.

When the prescription data 145 is generated by the prescription server 140, the prescription data 145 may be transmitted not only to the user equipment 100 but also to the diagnosis server 120, and may be additionally considered when the basic diagnostic data 130 and/or the diagnostic result data 135 are generated by the diagnosis server 120 at a later time.

Although for convenience of description, the diagnosis server 120 and the prescription server 140 are illustrated separately, the operation of the prescription server 140 may be included in the diagnosis server 120, and such an embodiment should be understood as being included in the scope of the present disclosure. In addition, although the medical server 160 is illustrated separately, the medical server 160 may be a concept included in the prescription server 140.

Figure 2:
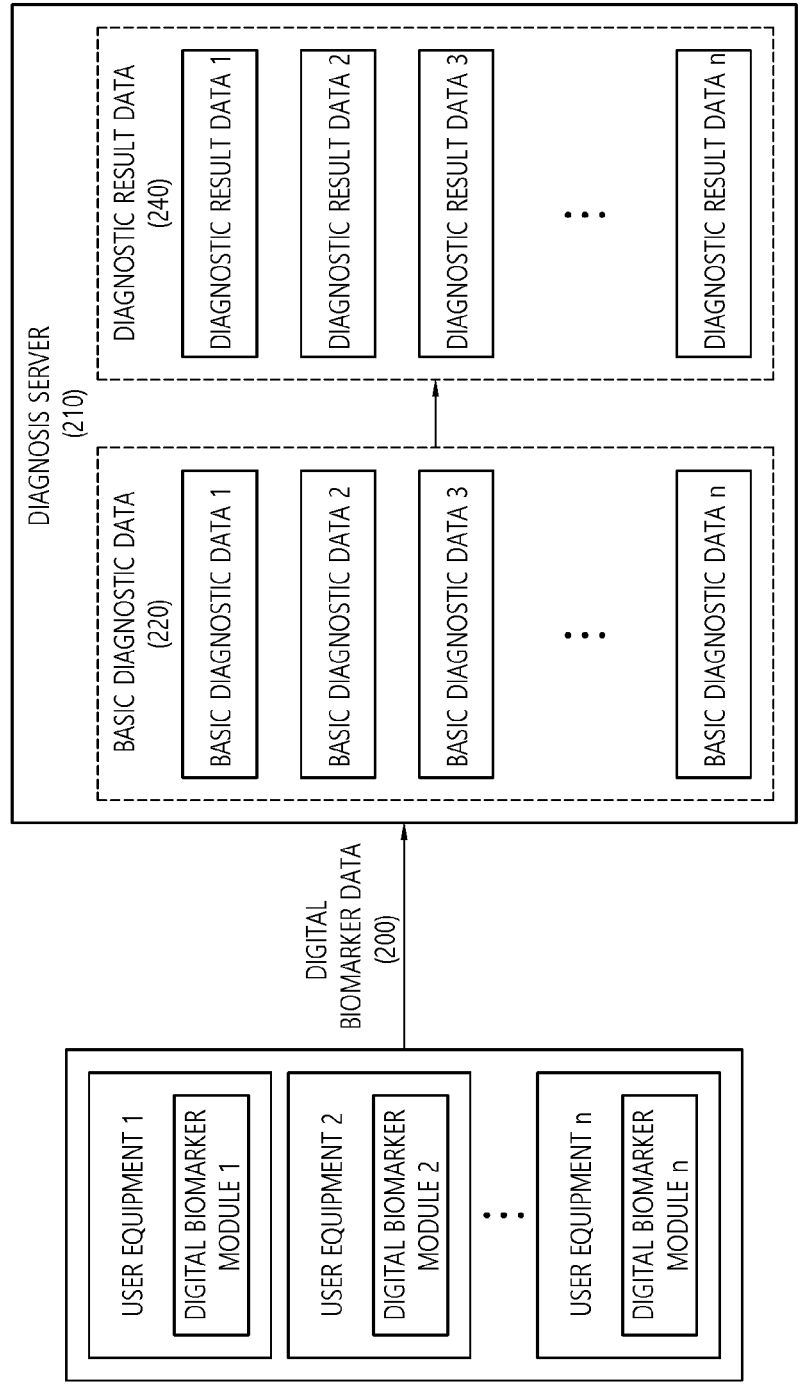
FIG. 2 is a conceptual diagram of a diagnosis method based on a digital biomarker according to an embodiment of the present disclosure.

FIG. 2 is a conceptual diagram of a diagnosis method based on a digital biomarker according to an embodiment of the present disclosure.

FIG. 2 is a conceptual diagram illustrating a method of generating digital biomarker data on the basis of user equipment and generating basic diagnostic data and diagnostic result data based on the digital biomarker data.

Referring to FIG. 2, user equipment 1, user equipment 2, ..., and user equipment n may be provided.

A digital biomarker module 1 to a digital biomarker module n may respectively correspond to the user equipment 1, the user equipment 2, ..., and the user equipment n. The types of digital biomarker modules corresponding to the multiple pieces of user equipment may be the same. A plurality of digital biomarker modules may correspond to one piece of user equipment.

Digital biomarker data 200 may be generated by each of the digital biomarker module 1 to the digital biomarker module n. When the types of the digital biomarker modules corresponding to the multiple pieces of user equipment are the same, the types of the digital biomarker data 200 may be the same.

The digital biomarker data 200 may be generated according to a user input received through user equipment, as well as digital biomarker modules.

A marker generated without an additional user input similar to a digital biomarker module such as a sensor may be classified as a digital biomarker (first type), and user input information which is input through user equipment may be classified as a digital biomarker (second type).

The digital biomarker data 200 may be transmitted to a diagnosis server 210, and basic diagnostic data 1 to basic diagnostic data n may be generated from the digital biomarker data 200 in the diagnosis server 210. A piece of the digital biomarker data 200 may be used to generate at least one piece of basic diagnostic data 220.

The diagnosis server 210 may generate diagnostic result data 240 on the basis of the basic diagnostic data 220, and the diagnostic result data 240 may be transmitted to a prescription server to be used for prescription. The diagnostic result data 240 may be used to generate a result of diagnosing a certain disease from at least one piece of the basic diagnostic data 220.

Figure 3:
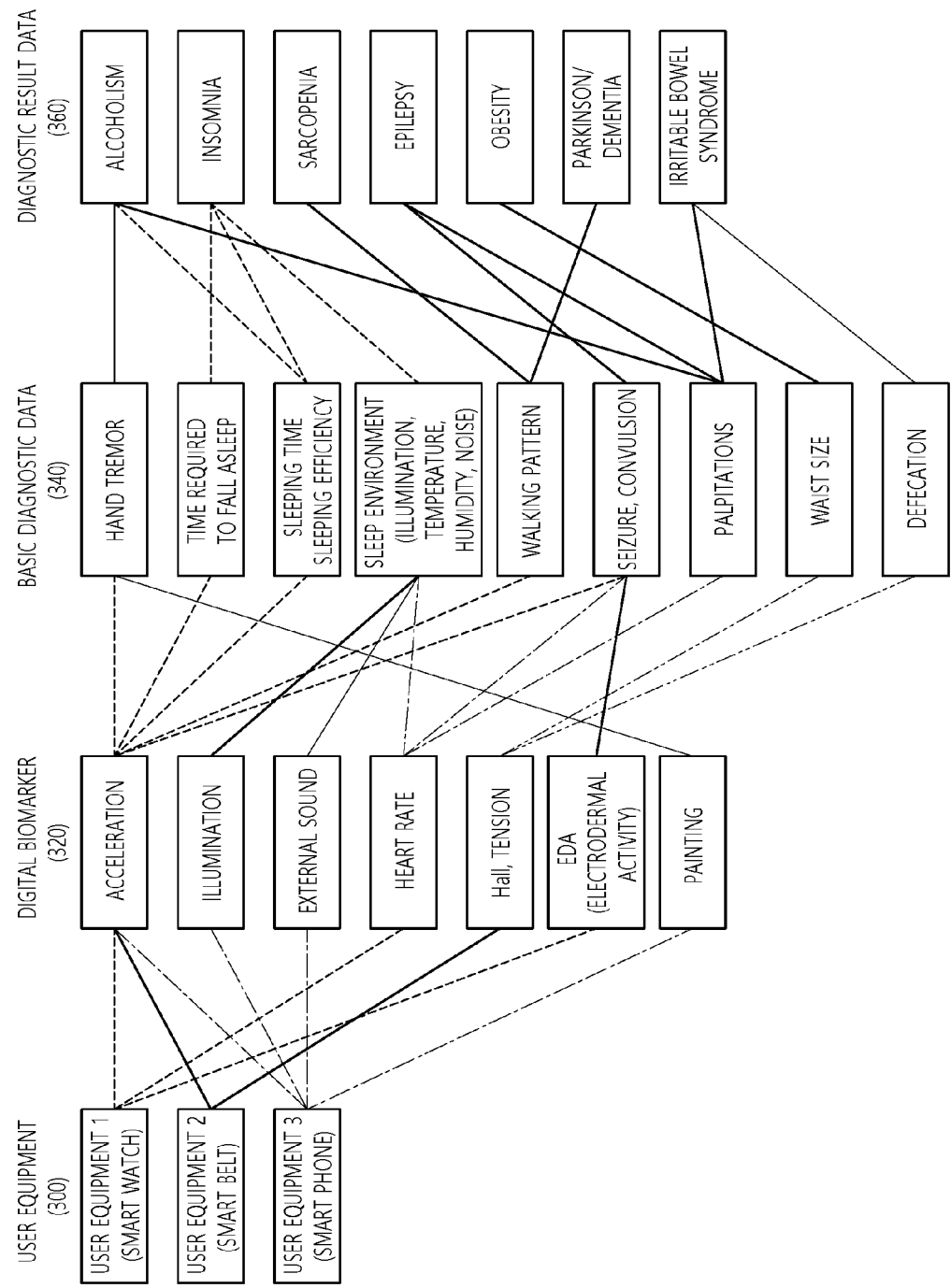
FIG. 3 is a conceptual diagram of a diagnosis method based on a digital biomarker according to another embodiment of the present disclosure.

FIG. 3 is a conceptual diagram of a diagnosis method based on a digital biomarker according to an embodiment of the present disclosure.

FIG. 3 illustrates a method of generating basic diagnostic data and diagnostic result data.

Referring to FIG. 3, a user equipment 300 may include user equipment 1, user equipment 2, and user equipment 3. The user equipment 1 may be a smart watch, the user equipment 2 may be a smart belt, and the user equipment 3 may be a smart phone.

The user equipment 1 (smart watch) may be put on a user's wrist, and include, as a digital biomarker module, an acceleration sensor, a heart rate sensor, an electrodermal activity sensor, or the like. A digital biomarker 320 obtained by the user equipment 1 (smart watch) may be an acceleration generated by the user, a heart rate, electrodermal activity or the like.

The user equipment 2 (smart belt) may be put on a user's waist, and include, as a digital biomarker module, an acceleration sensor, a Hall sensor (tension sensor) or the like. A digital biomarker 320 obtained by the user equipment 2 (smart belt) may be an acceleration generated by a user or a tension generated in the smart belt due to a waist size.

The user equipment 3 (smart phone) may be a mobile phone that a user carries, and include, as a digital biomarker module, an acceleration sensor, an illumination sensor, a microphone, or a display. A digital biomarker 320 obtained by the user equipment 3 (smart phone) may include an image (drawing) or the like generated due to an acceleration generated by a user, external light, external sound, or a touch.

A plurality of pieces of digital biomarker data corresponding to a plurality of digital biomarkers 320 generated by a plurality of pieces of user equipment (the user equipment 1, the user equipment 2, and the user equipment 3) may be transmitted to a diagnosis server, and the diagnosis server may generate basic diagnostic data 340 on the basis of each of the plurality of pieces of digital biomarker data.

1) Digital biomarker (acceleration and drawing) may generate hand tremor data as diagnostic basic data 340.

2) A digital biomarker (acceleration) may generate data about the time taken to fall asleep as basic diagnostic data 340.

3) A digital biomarker (acceleration) may generate sleeping time data and sleep efficiency data as basic diagnostic data 340.

4) Digital biomarkers (illumination, external sound, and a user's heart rate) may generate, as basic diagnostic data 340, sleeping environment data (sleep environment (illumination, temperature, humidity, and noise)).

5) A digital biomarker (acceleration) may generate walking pattern data as basic diagnostic data 340.

6) Digital biomarkers (acceleration, heart rate and electrodermal activity) may generate seizure/convulsion data as basic diagnostic data 340.

7) A digital biomarker (heart rate) may generate palpitation data as basic diagnostic data 340.

8) A digital biomarker (tension) may generate waist size data as basic diagnostic data 340.

9) A digital biomarker (tension) may generate defecation data (bowel movement time, the number of bowel movements) as basic diagnostic data 340.

Thereafter, the basic diagnostic data 340 may be used to generate diagnostic result data 360.

1) Basic diagnostic data (hand tremor data and palpitation data) may be used to generate diagnostic result data 360 about drug addiction and alcoholism.

2) Basic diagnostic data (data about a time taken to fall asleep, sleeping hours data, sleep efficiency data, and sleep environment data) may be used to generate diagnostic result data 360 about insomnia.

3) Basic diagnostic data (walking pattern data) may be used to generate diagnostic result data 360 about sarcopenia.

4) Basic diagnostic data (seizure/convulsion data and palpitation data) may be used to generate diagnostic result data 360 about epilepsy.

5) Basic diagnostic data (waist size data) may be used to generate diagnostic result data 360 about obesity.

6) Basic diagnostic data (walking pattern data) may be used to generate diagnostic result data 360 about Parkinson's disease/dementia.

7) Basic diagnostic data (palpitation data and defecation data) may be used to generate diagnostic result data 360 about irritable bowel syndrome.

The user equipment, the digital biomarker 320, the basic diagnostic data 340, and the diagnostic result data 360 may be related to one another as described above. FIG. 3 illustrates an example, and the relationship among the digital biomarker 320, the basic diagnostic data 340 and the diagnostic result data 360 may be established in other various ways.

Figure 4:
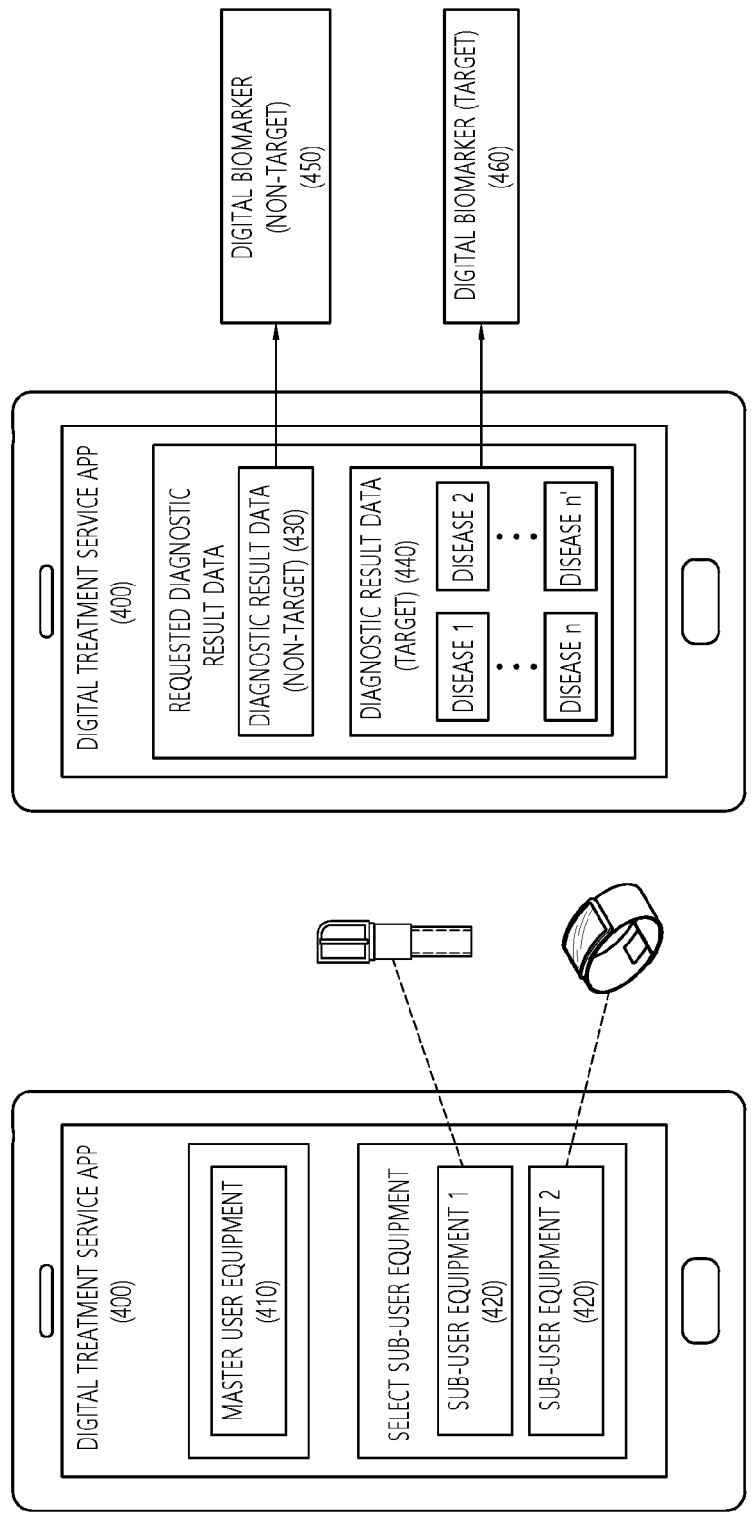
FIG. 4 is a conceptual diagram of a method of providing a digital treatment service through user equipment according to an embodiment of the present disclosure.

FIG. 4 is a conceptual diagram of a method of providing a digital treatment service through user equipment according to an embodiment of the present disclosure.

FIG. 4 illustrates a method of accessing a digital treatment service by user equipment when a digital treatment service is provided through the user equipment.

Referring to FIG. 4, when a digital treatment service application (APP) 400 is installed on user equipment and driven, information about a digital biomarker, which may be obtained on the basis of the user equipment, may be obtained.

User equipment in which the digital treatment service APP 400 is driven will be hereinafter referred to as master user equipment 410, and other pieces of user equipment connected to the master user equipment 410 will be hereinafter referred to as sub-user equipment 420.

Information regarding the sub-user equipment 420 connected to the master user equipment 410 may be obtained, and the types of digital biomarkers, which may be obtained on the basis of the sub-user equipment 420, as well as the master user equipment 410, may be displayed on a screen.

For example, when a user wears a smart phone, a smart watch, and a smart belt and the digital treatment service APP 400 is installed on the smartphone, the smartphone operating as the master user equipment 410 may identify, as pieces of sub-user equipment 420, the smart watch and the smart belt connected thereto through communication (e.g., Bluetooth).

Acceleration, illumination, sound, a heart rate, tension, electrodermal activity, drawing, etc., which are digital biomarkers obtainable on the basis of the smartphone, the smart watch, and the smart belt, may be displayed in the digital treatment service APP.

Digital biomarkers may be determined according to desired diagnostic result data on user equipment. Specified diagnostic result data may be diagnostic result data (target) 440, and unspecified diagnostic result data may be diagnostic result data (non-target) 430.

For example, when a user wants diagnostic result data about a certain disease (e.g., alcoholism), alcoholism may be selected as the diagnostic result data (target) 440. When alcoholism is selected, the diagnostic result data (target) 440 necessary for determination of alcoholism may be determined, and a digital biomarker (target) for generating the basic diagnostic data (target) may be determined. The basic diagnostic data (target) necessary for determination of alcoholism may be hand tremor data, palpitation data, etc., and the digital biomarker (target) for determining the basic diagnostic data (target) may be acceleration, drawing, a heart rate, etc.

A digital biomarker (target) 460 may be a digital biomarker for generating a basic diagnostic data (target). The basic diagnostic data (target) may be basic diagnostic data for generating the diagnostic result data (target) 440.

The diagnosis server may recommend an available digital biomarker (target) included in the digital biomarker (target) 460 among digital biomarkers obtainable on the basis of user equipment. The available digital biomarker (target) may be a digital biomarker corresponding to the digital biomarker (target) 460 among digital biomarkers obtainable through the user's user equipment. Thereafter, an available digital biomarker (target) 460 obtainable in the user equipment may be selected. Alternatively, an available digital biomarker (target) may be automatically selected by the diagnosis server without being selected by user equipment.

Conversely, when a user does not want diagnostic result data about a certain disease and wants general diagnostic result data, the diagnostic result data (non-target) 430 may be selected. When the diagnostic result data (non-target) 430 is selected, an agreed upon available digital biomarker (non-target) or available by user equipment may be determined among obtainable digital biomarkers. Thereafter, basic diagnostic data and the diagnostic result data (non-target) 430 may be generated based on the digital biomarker (non-target) 450. The basic diagnostic data (non-target) 430 may be basic diagnostic data generated based on the available digital biomarker (non-target). The digital biomarker (non-target) 450 may be a digital biomarker for generating the basic diagnostic data (non-target) 430. The diagnostic result data (non-target) 430 may be basic diagnostic data generated based on the available digital biomarker (non-target).

The diagnostic result data (target) 440 may be sequentially determined in the order of basic diagnostic data (target) and a digital biomarker (target), and thereafter, after an available digital biomarker (target) is determined, basic diagnostic data (target) and diagnostic result data (target) may be generated on the basis of the available digital biomarker (target).

The diagnostic result data (non-target) 430 may be generated in the order of an available digital biomarker (non-target), basic diagnostic data (non-target), and diagnostic result data (non-target).

An operation method of the diagnosis server for generating the diagnostic result data (target) 440 and the diagnostic result data (non-target) 430 will be described in detail below.

Figure 5:
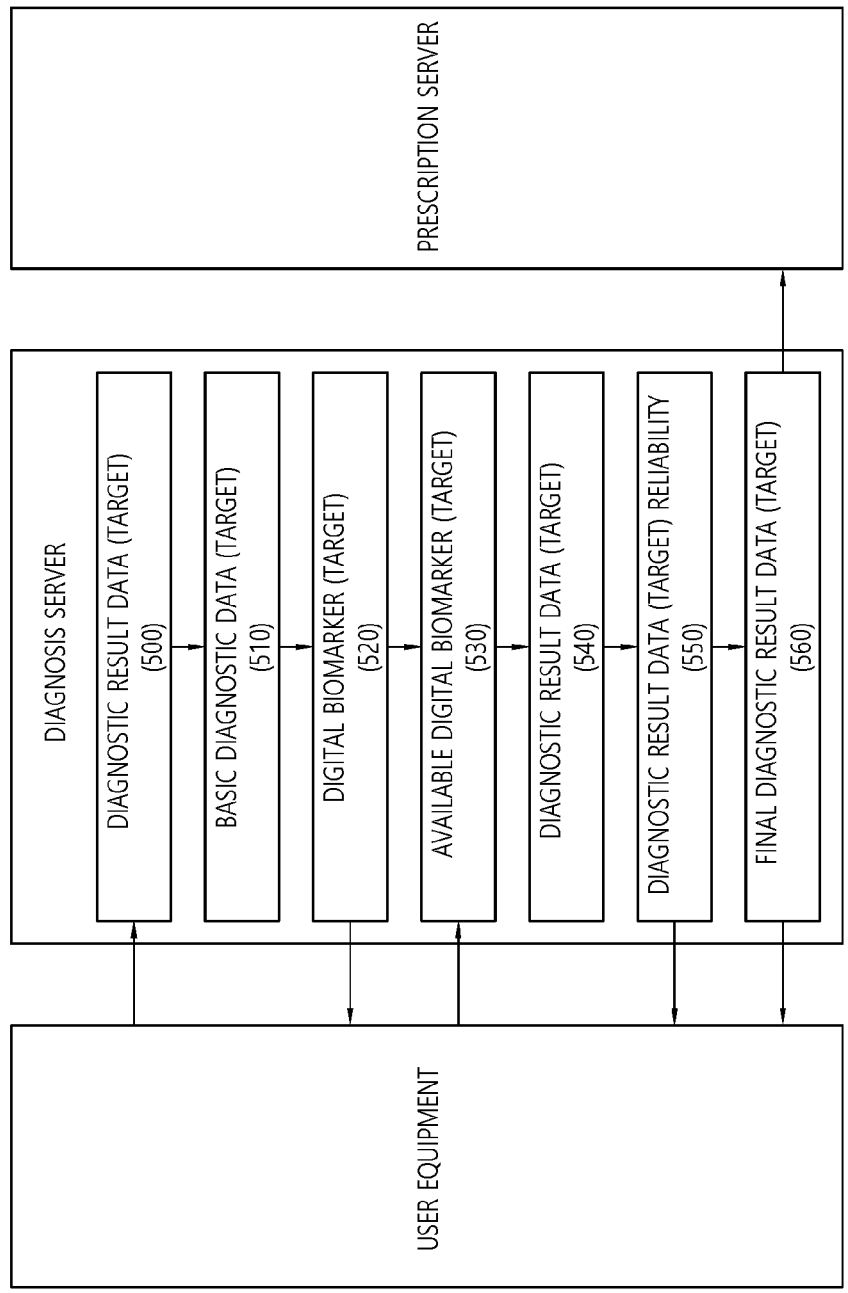
FIG. 5 is a conceptual diagram of a method of providing a digital treatment service through user equipment according to another embodiment of the present disclosure.

FIG. 5 is a conceptual diagram of a method of providing a digital treatment service through user equipment according to an embodiment of the present disclosure.

FIG. 5 illustrates a method of generating diagnostic result data (target).

Referring to FIG. 5, when diagnostic result data (target) 500 is selected, basic diagnostic data (target) 510 for generating the diagnostic result data (target) 500 may be determined, and digital biomarkers (targets) 520 for obtaining the basic diagnostic data 510 may be determined.

Among the digital biomarkers (targets) 520, an available digital biomarker (target) 530 obtainable on the basis of user equipment may be determined.

A diagnosis server may determine whether it is possible to obtain diagnostic result data (target) 500 with reliability equal to or greater than threshold reliability on the basis of the available digital biomarker (target) 530. Diagnostic result data (target) reliability 540 may be determined on the basis of information about an available digital biomarker (target) among digital biomarkers (targets) necessary to obtain certain diagnostic result data (target) 500.

For example, it may be assumed that the digital biomarkers (targets) 520 necessary for obtaining the diagnostic result data (target) 500 include a digital biomarker A (target), a digital biomarker B (target), and a digital biomarker C (target). When all of the digital biomarker A (target), the digital biomarker B (target) and the digital biomarker C (target) are available digital biomarkers (target) 530, the obtained diagnostic result data (target) 540 may have relatively high reliability 550. When there are only some of the digital biomarker A (target), the digital biomarker B (target) and the digital biomarker C (target), the obtained diagnostic result data (target) 540 may have relatively low reliability 550.

A reliability weight may be set to differently determine a reliability level according to the type of the digital biomarker (target) 520, and a higher reliability weight assigned to the digital biomarker (target) 520 may be used to determine more accurate diagnostic result data (target) 540.

The diagnosis server may provide only diagnostic result data (target) 540 with reliability equal to or greater than the threshold reliability as final diagnostic result data (target) 560. When only diagnostic result data (target) 540 with reliability less than or equal to a threshold set on the basis of the available digital biomarker (target) 530 is possible, the diagnosis server may transmit to the user equipment a message indicating that it is impossible to make a diagnosis to notify that the diagnostic result data (target) 540 is difficult to generate. In this case, information about digital biomarker (target) 520 additionally required to increase the reliability of the diagnostic result data (target) 540 may be transmitted in this message.

Alternatively, the diagnosis server may provide all diagnostic result data (target) 540 obtained on the basis of the available digital biomarker (target) 530 as final diagnostic result data (target) 560, together with information about reliability.

According to an embodiment of the present disclosure, a digital biomarker of the user equipment other than an available digital biomarker (target) may be activated to determine diagnostic result data (target) which is not selected by a user according to the set-up.

For example, when an available digital biomarker (target) is available to determine diagnostic result data (not selected) that is not been selected by the user, the available digital biomarker (target) may generate diagnostic result data (not selected). The diagnosis server may analyze the diagnostic result data (not selected) determined on the basis of the available digital biomarker (target), and an additional digital biomarker for generating more accurate diagnostic result data (not selected) may be activated to provide the diagnostic result data (not selected) to the user.

Figure 6:
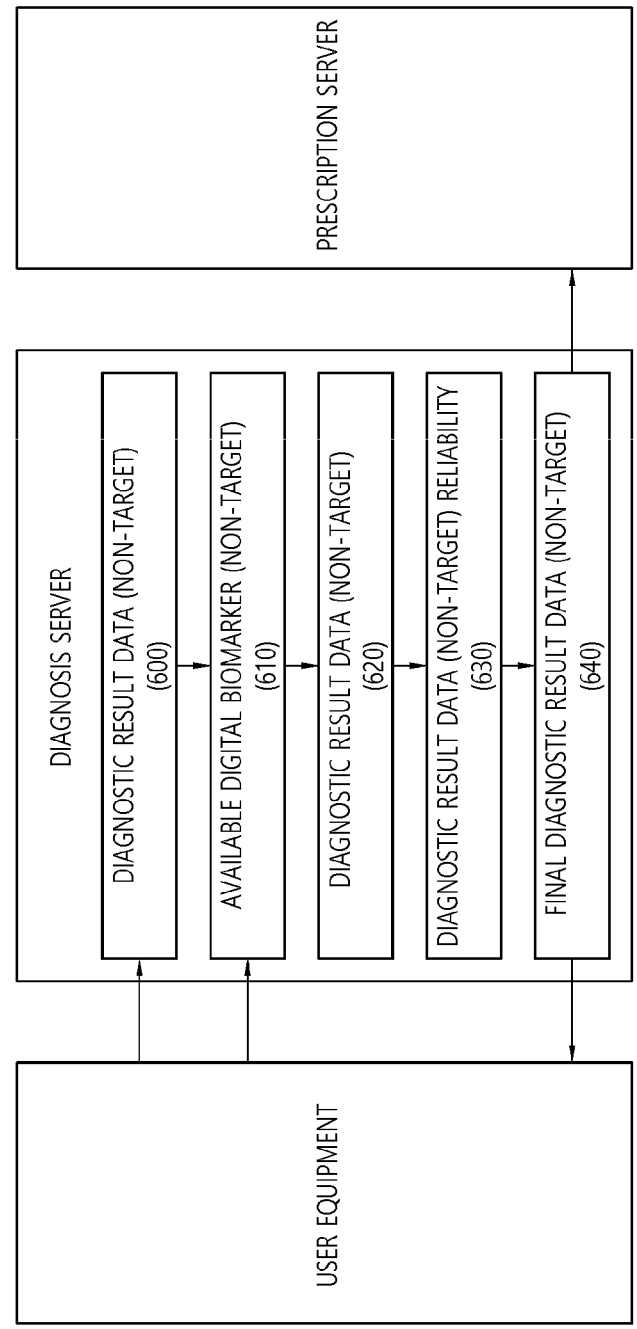
FIG. 6 is a conceptual diagram of a method of providing a digital treatment service through user equipment according to another embodiment of the present disclosure.

FIG. 6 is a conceptual diagram of a method of providing a digital treatment service through user equipment according to another embodiment of the present disclosure.

FIG. 6 illustrates a method of generating diagnostic result data (non-target).

Referring to FIG. 6, when diagnostic result data (non-target) 600 is selected, digital biomarkers (non-targets) for obtaining the diagnostic result data (non-target) 600 may be determined.

Unlike diagnostic result data (target), the digital biomarkers (non-targets) may be all available digital biomarkers (non-targets) 610 obtainable on the basis of user equipment.

A diagnosis server may determine diagnostic result data (non-target) 620 with reliability equal to or greater than threshold reliability on the basis of the available digital biomarkers (non-targets) 610. Diagnostic result data (non-target) reliability 630 may be determined on the basis of information about the available digital biomarkers (non-targets) 610.

It may be assumed that the available digital biomarkers (non-targets) 610 include a digital biomarker A (non-target), a digital biomarker B (non-target), and a digital biomarker C (non-target). The diagnosis server may determine diagnostic result data (non-target) 620 with reliability equal to or greater than the threshold reliability among diagnostic result data (non-target) 620 obtainable on the basis of the available digital biomarkers (non-targets) 610.

According to an embodiment of the present disclosure, the diagnosis server may determine only the diagnostic result data (non-target) 620 with reliability equal to or greater than the critical reliability, and transmit the diagnostic result data (non-target) 620 as final diagnostic result data (non-target) 640 to the user equipment.

Alternatively, the diagnosis server may provide all of the diagnostic result data (non-target) 600, which is obtained on the basis of the available digital biomarkers (non-targets) 610, as the final diagnostic result data (non-target) 640, together with information about reliability.

According to an embodiment of the present disclosure, the final diagnostic result data (non-target) 640 may be determined by performing reliability correction on diagnostic result data (non-target) 620 with reliability less than the threshold reliability and accumulated over time.

The diagnosis server may generate and analyze diagnostic result data (non-target) 620 with reliability less than the threshold reliability. The reliability of the diagnostic result data (non-target) 620 may be corrected to a relatively high level when a result of analyzing the diagnostic result data (non-target) 620 with reliability less than the threshold reliability reveals that it is possible to perform reliability correction, and the diagnostic result data (non-target) 620 may be transmitted to the user equipment when the reliability of the diagnostic result data (non-target) 620 is equal to or greater than the threshold reliability.

For example, when the diagnostic result data (non-target) 620 with reliability less than the threshold reliability is accumulated over time and the reliability of the accumulated diagnostic result data 620 is the same or continuously shows a certain tendency, the reliability of the diagnostic result data (non-target) 620 with reliability less than the threshold reliability may be corrected and the diagnostic result data 620 may be transmitted as final diagnostic result data (non-target) 640 when the reliability thereof is equal to or greater than the threshold reliability as a result of the correction.

The tendency of the diagnostic result data (non-target) 620 with reliability less than the threshold reliability may be the same as a result of performing a diagnosis on the basis of the accumulated diagnostic result data (non-target) 620.

Figure 7:
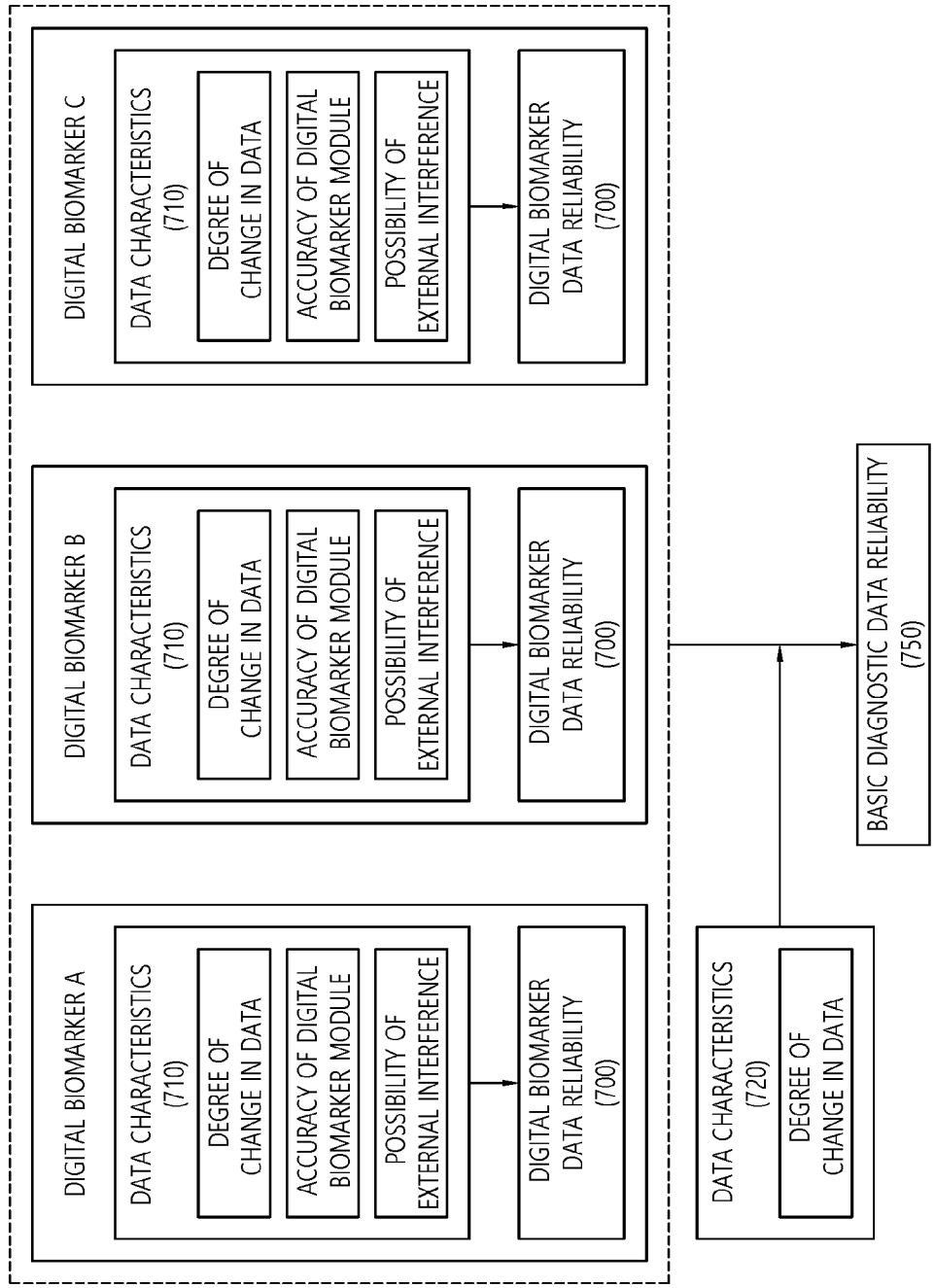
FIG. 7 is a conceptual diagram of a method of generating diagnostic result data according to an embodiment of the present disclosure.

FIG. 7 is a conceptual diagram of a method of generating diagnostic result data according to an embodiment of the present disclosure.

FIG. 7 illustrates a method of determining the reliability of diagnostic result data.

Referring to FIG. 7, as described above, the reliability of the diagnostic result data may be determined on the basis of a used digital biomarker but may be determined in further consideration of digital biomarker data reliability 700 provided through the digital biomarker, basic diagnostic data reliability 750 determined based on the digital biomarker data, and the like.

The digital biomarker data reliability 700 and the basic diagnostic data reliability 750 may be determined on the basis of various factors.

For example, the digital biomarker data reliability 700 may be determined in consideration of data characteristics 710. A threshold for determining the digital biomarker data reliability 700 may be adjusted according to the data characteristics 710.

For example, the data characteristics 710 of digital biomarker data may include a degree of change in data, digital biomarker module accuracy, the possibility of external interference, and the like. The degree of change in data refers to an average range of change of digital biomarker data, and the higher the degree of change in data, the greater an average degree of change in data. The digital biomarker module accuracy refers to the accuracy of a digital biomarker module such as a sensor that generates digital biomarker data, and the possibility of external interference refers to the possibility of inclusion of noise due to external interference during generation of digital biomarker data.

The basic diagnostic data reliability 750 may be determined in consideration of at least one piece of digital biomarker data reliability 700 for determining basic diagnostic data, and a weight may be additionally assigned to each piece of the at least one piece of digital biomarker data reliability 700 for determining basic diagnostic data.

When a plurality of digital biomarkers are used to generate basic diagnostic data, there may be a digital biomarker that has an influence on the basic diagnostic data or that is relatively important for generation of the basic diagnostic data among the plurality of digital biomarkers, and the basic diagnostic data reliability 750 may be determined by setting a relatively higher weight for the reliability of such a digital biomarker.

Similar to the digital biomarker data, the basic diagnostic data reliability 750 may be determined by taking into further consideration the data characteristics 720 of the basic diagnostic data. The data characteristics 720 of the basic diagnostic data may include a degree of change in data. The degree of change in data refers to an average range of change in basic diagnostic data, and the higher the degree of change in data, the greater an average degree of change in data.

Figure 8:
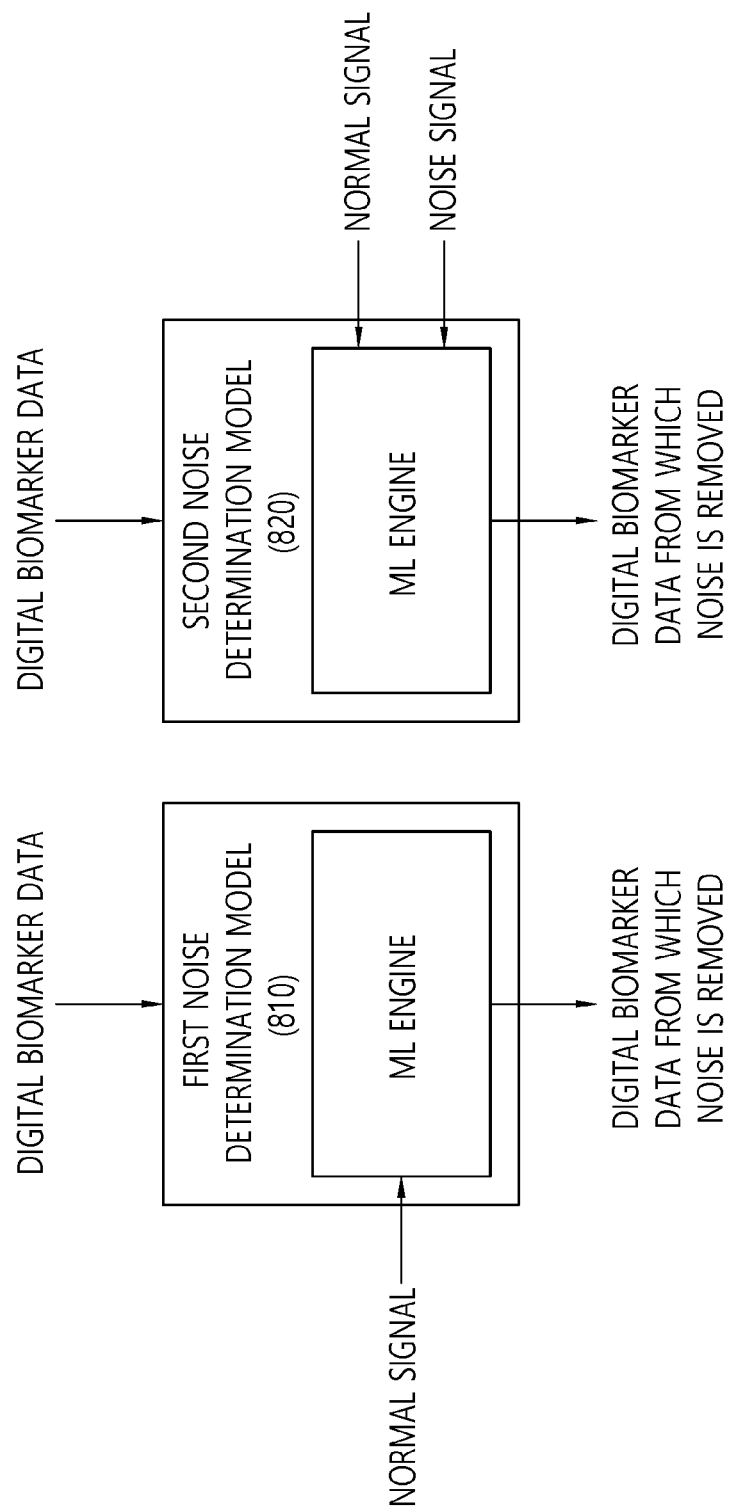
FIG. 8 is a conceptual diagram of a method of generating basic diagnostic data according to an embodiment of the present disclosure.

FIG. 8 is a conceptual diagram of a method of generating basic diagnostic data according to an embodiment of the present disclosure.

FIG. 8 illustrates a method of generating basic diagnostic data by removing noise from digital biomarker data.

Referring to FIG. 8, a diagnosis server may identify whether obtained data is noise to remove noise from digital biomarker data and basic diagnostic data.

The diagnosis server may identify whether an obtained value is noise on the basis of a data pattern of the digital biomarker data. The diagnosis server may be trained with a data pattern with respect to a plurality of periods to learn a plurality of data patterns of the digital biomarker data. Data input for training the data pattern may be various pieces of data that may be generated in a normal measurement situation. An abnormal data pattern may be detected on the basis of a result of training with respect to the plurality of periods and a current data pattern of the digital biomarker data, and classified as noise to additionally perform learning.

According to an embodiment of the present disclosure, two noise determination models (a first noise determination model 810 and a second noise determination model 820) may be used to extract noise data.

The first noise determination model 810 is a model that identifies noise by learning without additionally classifying noise, and the second noise determination model 820 is a model that identifies noise by additionally performing classification of noise and then performs learning.

In the first noise determination model 810 according to an embodiment of the present disclosure, learning may be performed through classification of normal signals other noise signals without classifying and learning noise signals. That is, neural-network-based learning may be performed with respect to only normal signals to learn a weight for the normal signals, and all signals that are not normal signals may be classified as noise signals on the basis of the learning. When such a learning method is used, a noise-resistant model is generated rather than a method of performing learning by assigning an additional class to noise signals, thereby improving the noise filtering performance of a noise classification model.

In the second noise determination model 820 according to an embodiment of the present disclosure, noise signals may be classified and learned, and learning of classifying noise signals and normal signals may be performed. That is, neural-network-based learning may be performed for each of noise signals and normal signals to learn weights for the normal signals and the noise signals, and the normal signals and the noise signals may be classified based on the learning.

In the present disclosure, noise may be identified by selectively applying the first noise determination model 810 or the second noise determination model 820 according to data characteristics of digital biomarker data.

The diagnosis server may continuously collect data patterns of digital biomarker data obtained through user equipment and may be trained with the data patterns to additionally learn various data patterns that may occur in various situations, thereby improving the accuracy of identifying abnormal data patterns. The diagnosis server may use a data pattern occurring in each situation as digital biomarker data according to the situation without performing noise processing on the data pattern. That is, when it is possible to accurately identify a situation in which an abnormal data pattern occurs, digital biomarker data identified as a corresponding abnormal data pattern may be corrected according to the situation and used as normal data to generate basic diagnostic data.

Figure 9:
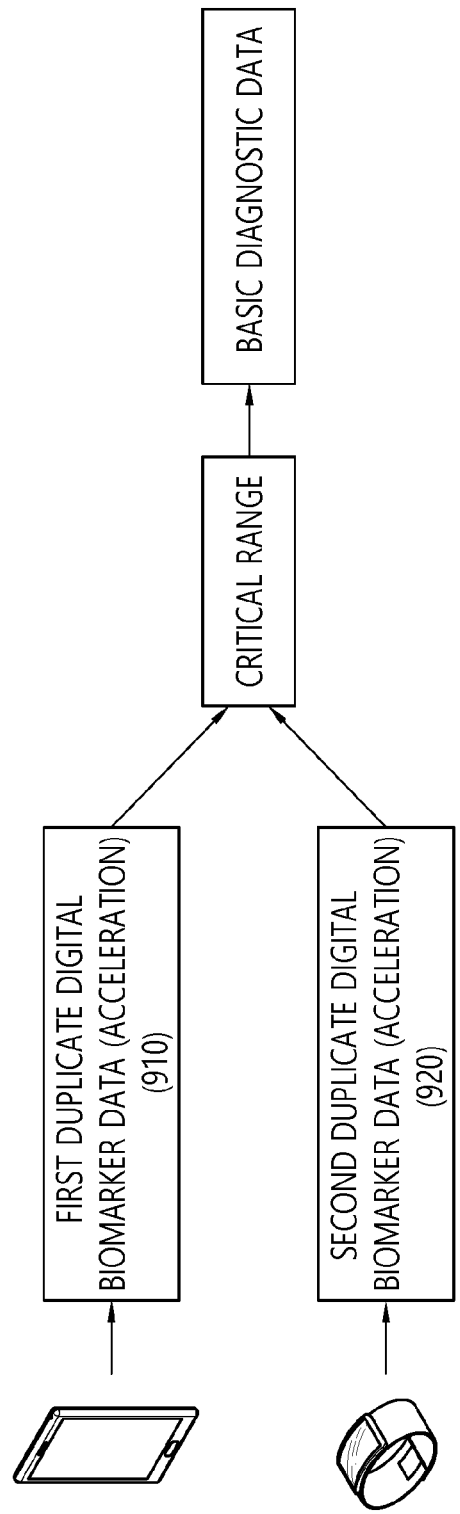
FIG. 9 is a conceptual diagram of a method of generating basic diagnostic data according to another embodiment of the present disclosure.

FIG. 9 is a conceptual diagram of a method of generating basic diagnostic data according to another embodiment of the present disclosure.

FIG. 9 illustrates a method of generating basic diagnostic data when the same pieces of digital biomarker data are simultaneously obtained.

Referring to FIG. 9, when the same pieces of digital biomarker data are simultaneously obtained, basic diagnostic data may be generated by processing the same pieces of digital biomarker data. For example, it may be assumed that a user uses both a smart phone and a smart watch as pieces of user equipment. Acceleration data may be obtained as digital biomarker data at the same point of time by both the smart phone and the smart watch. The same pieces of digital biomarker data obtained at the same point of time may be referred to as duplicate digital biomarker data.

When a plurality of pieces of duplicate digital biomarker data are generated, duplicate digital biomarker data of a section in which noise is present among the plurality of pieces of duplicate digital biomarker data may be excluded.

Thereafter, whether there is a similarity in a critical range may be determined on the basis of, as a reference value, a value of a plurality of pieces of duplicate biomarker data in a section in which noise is not present. For example, when first duplicate digital biomarker data (acceleration) 910 is obtained by a smart phone and second duplicate digital biomarker data (acceleration) 920 is obtained by a smart watch, whether the difference between the first duplicate digital biomarker data (acceleration) 910 and the second duplicate digital biomarker data (acceleration) 920 is within a critical range may be determined, and duplicate digital biomarker data with higher reliability may be selected as basic diagnostic data.

Conversely, when the difference between the first duplicate digital biomarker data (acceleration) 910 and the second duplicate digital biomarker data (acceleration) 920 is beyond the critical range, whether abnormal data occurs may be determined with respect to another biomarker (or another digital biomarker module) obtainable on the basis of user equipment. When abnormal data occurs with respect to another biomarker (or another digital biomarker module) of certain user equipment, basic diagnostic data may be generated on the basis of remaining duplicate digital biomarker data except duplicate digital biomarker data generated by the user equipment.

When abnormal data does not occur with respect to the other biomarker of the user equipment, basic diagnostic data may be determined excluding a section in which the difference between the first duplicate digital biomarker data (acceleration) 910 and the second duplicate digital biomarker data (acceleration) 920 is beyond the critical range.

Alternatively, according to an embodiment of the present disclosure, when the difference between the first duplicate digital biomarker data 910 and the second duplicate digital biomarker data 920 is beyond the critical range, a piece of duplicate digital biomarker data may be determined on the basis of an additional digital biomarker (second type). As described above, the additional digital biomarker (second type) may be user response data obtained by asking the user a question through the user equipment. A question for selecting the first duplicate digital biomarker data 910 or the second duplicate digital biomarker data 920 is transmitted through the user equipment, and a duplicate digital biomarker may be determined based on the additional digital biomarker data (second type) including a response from the user.

Figure 10:
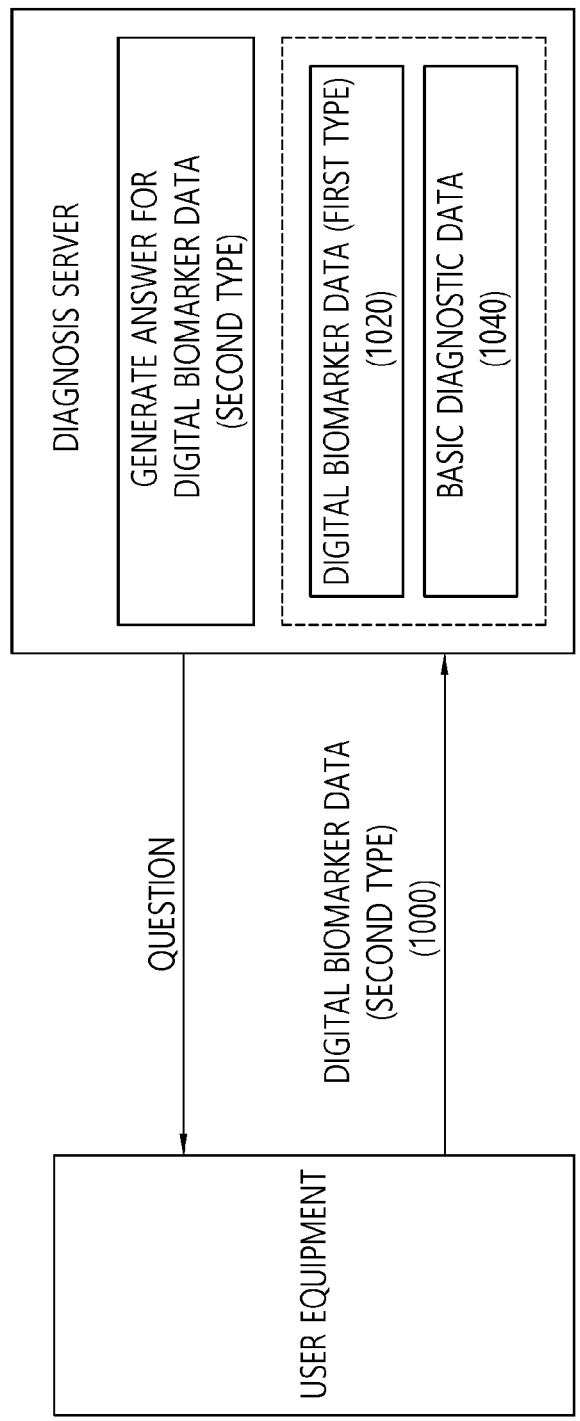
FIG. 10 is a conceptual diagram of a method of obtaining a digital biomarker (second type) on the basis of questions and answers with a user according to an embodiment of the present disclosure.

FIG. 10 is a conceptual diagram of a method of obtaining a digital biomarker (second type) on the basis of questions and answers with a user according to an embodiment of the present disclosure.

FIG. 10 illustrates a method of obtaining a digital biomarker on the basis of a question and answer with a user.

Referring to FIG. 10, digital biomarker data may be obtained not only through a sensor such as a digital biomarker module but also questions and answers with a user through user equipment. Digital biomarker data obtained based on user input data through questions and answers with a user may be referred to as digital biomarker data (second type) 1000.

When digital biomarker data (first type) 1020 and basic diagnostic data 1040 need to be checked or corrected, a diagnosis server may generate a question for obtaining the digital biomarker data (second type) 1000 and receive the digital biomarker data (second type) 1000.

When the digital biomarker data (second type) 1000 is received, the digital biomarker data (first type) 1020 and the basic diagnostic data 1040 may be checked or corrected on the basis of the digital biomarker data (second type) 1000.

The question for obtaining the digital biomarker data (second type) 1000 generated by the diagnosis server is a question for checking or correcting the digital biomarker data (first type) 1020 and the basic diagnostic data 1040 and may be automatically generated. For example, when it is necessary to check digital biomarker data (acceleration) obtained at 10 o'clock, a question asking whether you are going to bed at 10 o'clock may be automatically generated and provided to the user equipment, and the user may input, to the diagnosis server, an answer to the question as the digital biomarker data (second type) 1000.

Figure 11:
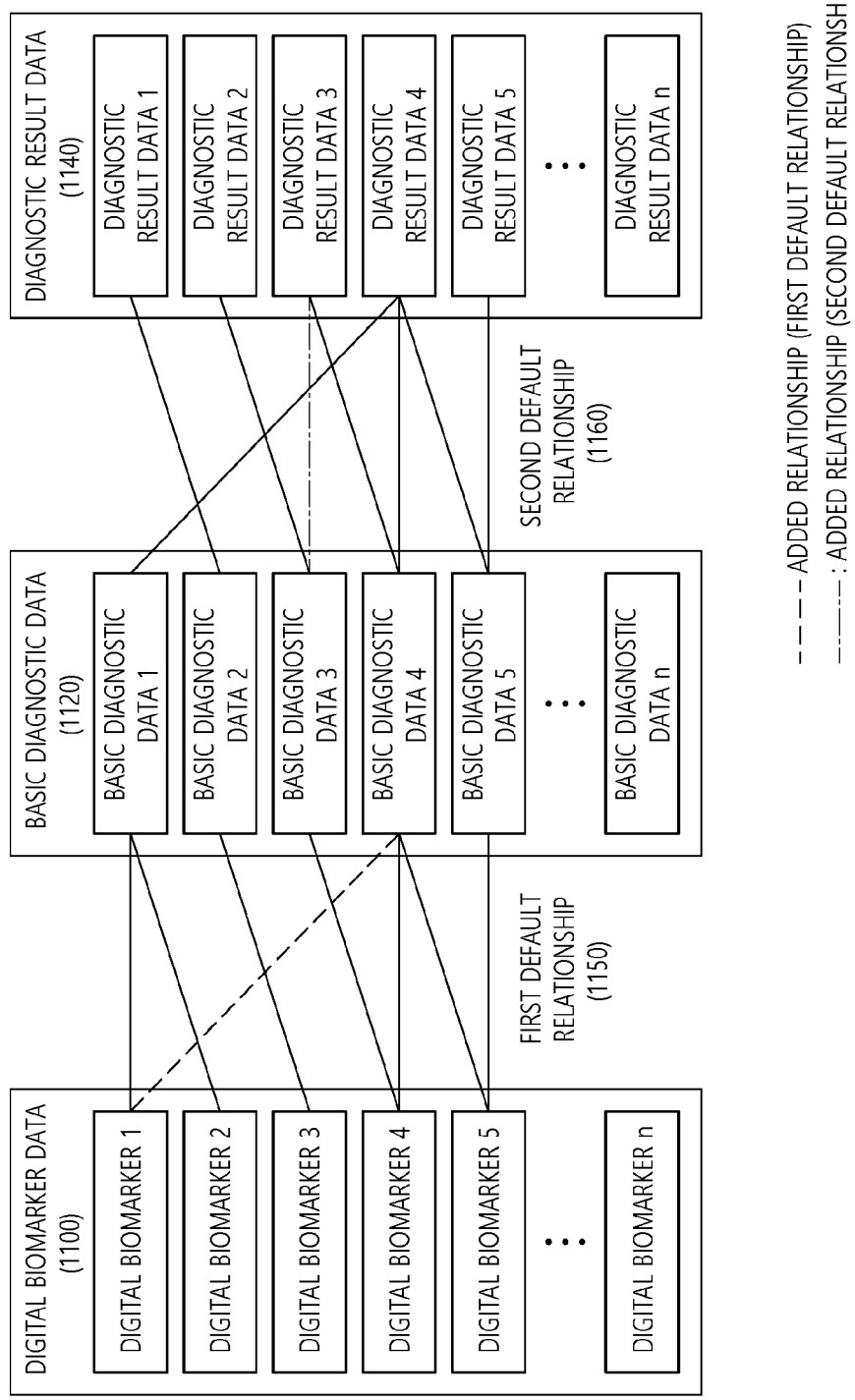
FIG. 11 is a conceptual diagram of a method of generating diagnostic result data by a diagnosis server according to an embodiment of the present disclosure.

FIG. 11 is a conceptual diagram illustrating a method of generating diagnostic result data by a diagnosis server according to an embodiment of the present disclosure.

Referring to FIG. 11, a diagnosis server may establish a relationship between digital biomarker data 1100 and basic diagnostic data 1120 and a relationship between the basic diagnostic data 1120 and diagnostic result data 1140.

There may be a first default relationship 1150 between the digital biomarker data 1100 and the basic diagnostic data 1120 and a second default relationship 1160 between the basic diagnostic data 1120 and the diagnostic result data 1140 as default relationships.

The diagnosis server may be trained with the relationships among the digital biomarker data 1100, the basic diagnostic data 1120, and the diagnostic result data 1140, which are collected from a plurality of pieces of user equipment, to modify or reset the first default relationship 1150 and the second default relationship 1160.

Specifically, in order to modify the first default relationship 1150, the diagnosis server may collect information about other digital biomarkers in addition to the first default relationship 1150 and may be trained with the relationship between digital biomarker data and basic diagnostic data.

For example, it is assumed that a first default relationship is established among a digital biomarker A, a digital biomarker B and basic diagnostic data X, and basic diagnostic data C is determined based on the digital biomarker data A and the digital biomarker data B.

In this case, a relationship among other digital biomarkers (e.g., a digital biomarker C, a digital biomarker D, etc.) and the basic diagnostic data C may be learned on the basis of digital biomarkers collected through user equipment, and the digital biomarker D may be added to modify the first default relationship 1150 when it is determined that there is a relationship between a certain digital biomarker (e.g., the digital biomarker D) and the basic diagnostic data C.

Similarly, in order to modify the second default relationship 1160, the diagnosis server may collect another piece of basic diagnostic data 1120 in addition to the second default relationship 1160, and may then be trained with the relationship between the basic diagnostic data 1120 and the diagnostic result data 1140.

For example, it is assumed that a second default relationship is established between basic diagnostic data E, basic diagnostic data F, and diagnostic result data G, and the diagnostic result data G is determined based on the basic diagnostic data E and the basic diagnostic data F.

In this case, the relationship between other pieces of basic diagnostic data (e.g., basic diagnostic data H and basic diagnostic data I) and basic diagnostic data G may be learned, and the basic diagnostic data H may be added to modify the second default relationship 1160 when it is determined that there is a relationship between certain basic diagnostic data (e.g., the basic diagnostic data H) and the diagnostic result data G.

An initial reliability of an additional digital biomarker newly added to correct the first default relationship 1150 may be set according to a degree of relationship but may be set to a relatively low value at an initial stage, and the reliability of the additional digital biomarker may be determined to be a value greater than the initial reliability when it is determined that the relationship is continuously present during an additional threshold period.

Similarly, an initial reliability of additional basic diagnostic data newly added to correct the second default relationship 1160 may be set according to a degree of relationship but may be set to a relatively low value, and the reliability of the additional basic diagnostic data may be determined to be a value greater than the initial reliability when it is determined that the relationship is continuously present during an additional threshold period.

That is, according to an embodiment of the present disclosure, the diagnosis server may continuously track and/or may be trained with the digital biomarker data 1100, the basic diagnostic data 1120, and the diagnostic result data 1140, and may adaptively reset the relationship between the digital biomarker data 1100 and the basic diagnostic data 1120 and the relationship between the basic diagnostic data 1120 and the diagnostic result data 1140.

Figure 12:
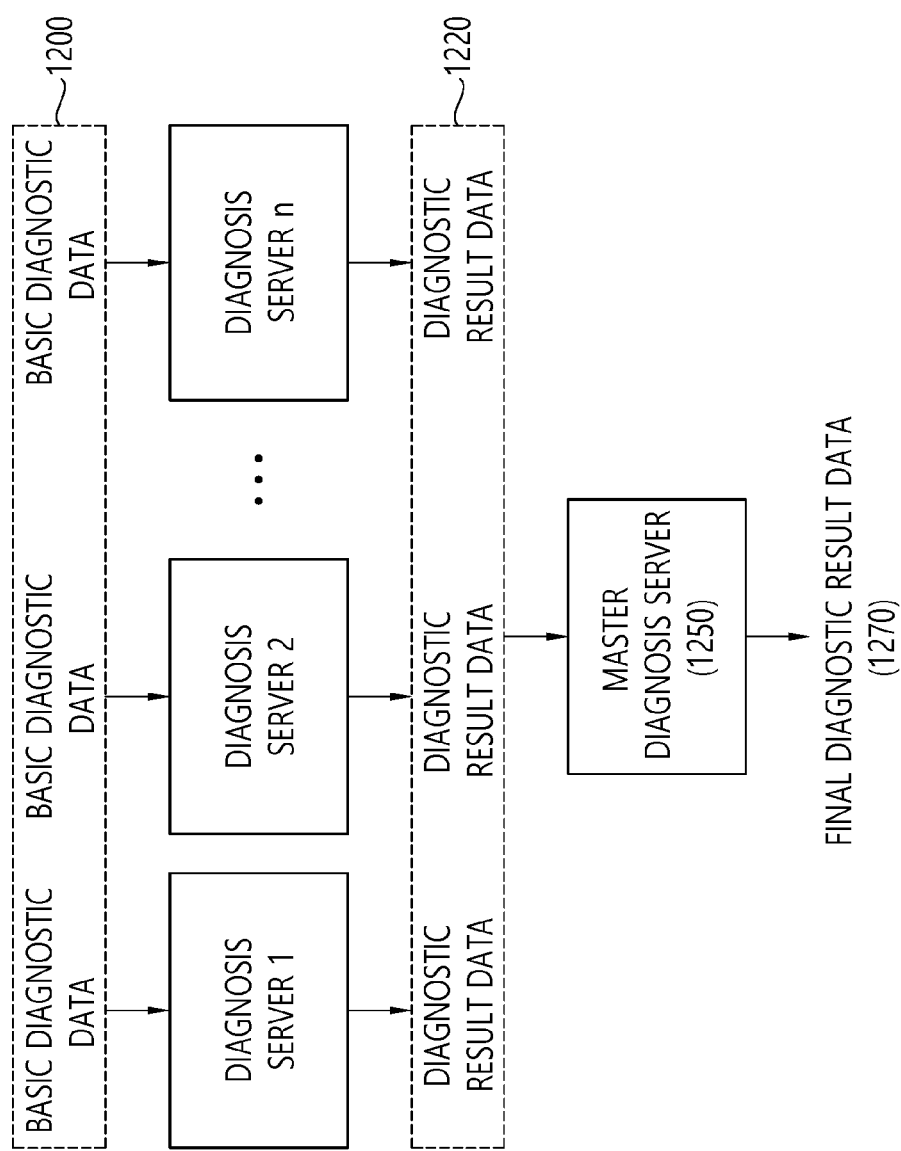
FIG. 12 is a conceptual diagram of the operation of a diagnosis server according to an embodiment of the present disclosure.

FIG. 12 is a conceptual diagram of an operation of a diagnosis server according to an embodiment of the present disclosure.

FIG. 12 illustrates an operation of a diagnosis server for generating diagnostic result data.

Referring to FIG. 12, a diagnosis server may generate diagnostic result data 1220 on the basis of basic diagnostic data 1200.

The diagnosis server may generate the diagnostic result data 1220 on the basis of a diagnostic result generation algorithm. There may be one diagnosis server and the diagnosis server may generate and transmit a piece of diagnostic result data 1220 but a plurality of diagnosis servers may generate a plurality of pieces of diagnostic result data 1220.

According to an embodiment of the present disclosure, a plurality of diagnosis servers may be provided to generate diagnostic result data 1220, and each of the plurality of diagnosis servers may generate each of a plurality of pieces of diagnostic result data 1220 on the basis of the same basic diagnostic data 1200. Each of the plurality of diagnosis servers may generate each of the plurality of diagnostic result data 1220 by analyzing the basic diagnostic data 1200 using an individual diagnosis algorithm.

User equipment may select a certain diagnosis server to receive the diagnostic result data 1220, or one master diagnosis server may be provided to analyze the diagnostic result data 1220 received from the plurality of diagnosis servers and provide a result of the analyzing as final diagnostic result data 1270 to the user equipment.

A master diagnosis server 1250 may analyze the plurality of pieces of diagnostic result data 1220 from the plurality of diagnosis servers, analyze the plurality of pieces of diagnostic result data 1220, and transmit diagnostic result data 1220 with high reliability to the user equipment.

The master diagnosis server 1250 may analyze the accuracy of the diagnostic result data 1220 from each of the plurality of diagnosis servers with respect to a certain target disease, the accuracy of the diagnostic result data 1220 from each of the plurality of diagnosis servers with respect to the target disease according to data characteristics (the amount of collected data, the reliability of the collected data, the user equipment used to collect the data, and user characteristic information), and the like.

The master diagnosis server 1250 may combine the plurality of pieces of diagnostic result data 1220 generated by the plurality of diagnosis servers to increase the accuracy of the diagnostic result data 1220, and transmit a result of the combination as final diagnostic result data 1270 to the user equipment.

Figure 13:
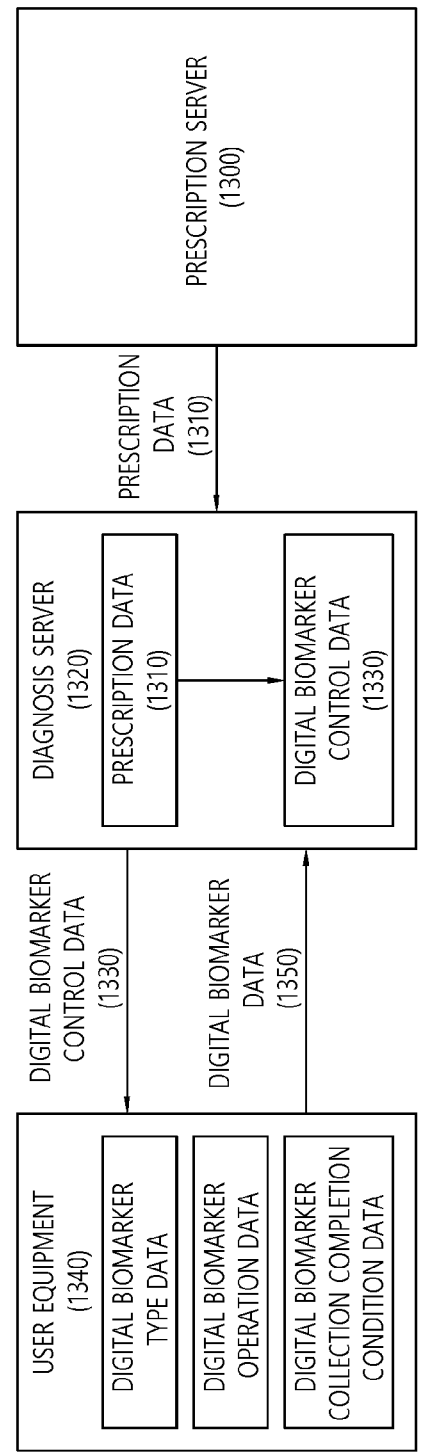
FIG. 13 is a conceptual diagram of an operation of a user health diagnosis system based on prescription data according to an embodiment of the present disclosure.

FIG. 13 is a conceptual diagram of an operation of a user health diagnosis system based on prescription data according to an embodiment of the present disclosure.

FIG. 13 illustrates a method of re-performing a user health diagnosis by a user health diagnosis system on the basis of a feedback on prescription data.

Referring to FIG. 13, user-specific prescription data 1310 is fed back to the user health diagnosis system to regenerate digital biomarker data, basic diagnostic data, and diagnostic result data for a user so as to generate new prescription data according to the user's condition.

For example, when prescription data 1310 for a user who has been diagnosed as having alcoholism is generated by a prescription server 1300, the prescription data 1310 may be transmitted to a diagnosis server 1320. The diagnosis server 1320 may generate digital biomarker control data 1330 for controlling the operation of user equipment 1340 for collecting digital biomarker data according to the prescription data 1310, and transmit the digital biomarker control data 1330 to the user equipment 1340. Data for controlling the operation of the user equipment 1340 for collecting digital biomarkers according to the prescription data 1310 may be referred to as the digital biomarker control data 1330. The user equipment 1340 may generate digital biomarker data 1350 on the basis of the digital biomarker control data 1330 and transmit the digital biomarker data 1350 to the diagnosis server 1320, and the diagnosis server 1320 may generate basic diagnostic data and diagnostic result data for generating new prescription data 1310.

The digital biomarker control data 1330 may include digital biomarker type data, digital biomarker operation data, and/or digital biomarker collection completion condition data for generating diagnostic result data.

The digital biomarker type data may include information on the type of digital biomarker to be used to regenerate prescription data. The digital biomarker type data may include information regarding a digital biomarker that has been used previously or information regarding a newly added or modified digital biomarker.

The digital biomarker operation data may include information regarding the operation of a digital biomarker module for obtaining digital biomarker data. The digital biomarker operation data may include information regarding an operation cycle, an operation period, and the amount of collected data of the digital biomarker module.

The digital biomarker collection completion condition data may include information regarding a condition for completing collection of digital biomarker data for regenerating prescription data. For example, the digital biomarker collection completion condition data may include information such as a collection period, amount, and reliability of digital biomarker data.

Prescription data 1310 generated first with respect to a user's specific diagnostic result data (target) may be prescription data (first round), and prescription data 1310 regenerated according to a continuous prescription may be sequentially prescribed data ($n^{th}$ round) (here, n is a natural number equal to or greater than 2).

The digital biomarker control data 1330 may also be changed according to the number of times the prescription data 1310 is generated. For example, prescription data 1310 for a user who has been diagnosed as having alcoholism may be periodically generated according to diagnostic result data that is periodically generated. Periodically generated prescription data 1310 may be periodically transmitted to the diagnosis server 1320, and the diagnosis server 1320 may generate digital biomarker control data 1330 periodically and on the basis of diagnostic result data and the number of times that prescription data is generated.

Figure 14:
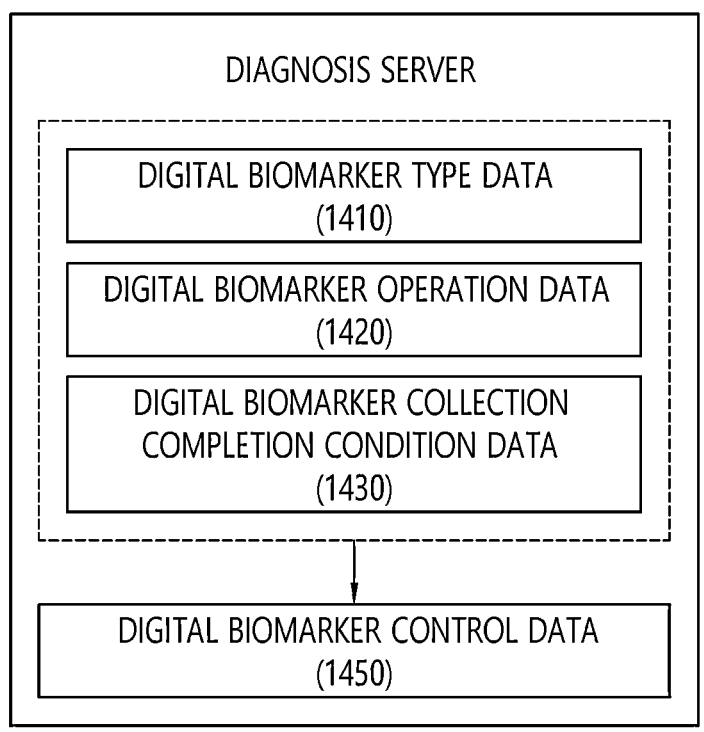
FIG. 14 is a conceptual diagram of a method of generating digital biomarker control data according to an embodiment of the present disclosure.

FIG. 14 is a conceptual diagram of a method of generating digital biomarker control data according to an embodiment of the present disclosure.

FIG. 14 illustrates a method of generating digital biomarker control data.

Referring to FIG. 14, when a prescription server generates prescription data with respect to a certain disease, the diagnosis server may generate digital biomarker control data (the digital biomarker type data 1410, the digital biomarker operation data 1420 and/or the digital biomarker collection completion condition data 1430, etc.).

A method of generating the digital biomarker type data 1410 as digital biomarker control data by the diagnosis server will be described below.

The diagnosis server may determine whether diagnostic result data with reliability equal to or greater than threshold reliability is obtainable by user equipment on the basis of currently available digital biomarker data. The threshold reliability may be adjusted adaptively according to the user's diagnostic result data.

When diagnostic result data with reliability equal to or greater than the threshold reliability is obtainable on the basis of the currently available digital biomarker data, the digital biomarker type data may include information regarding the currently available digital biomarker.

In contrast, when it is difficult to obtain diagnostic result data with reliability equal to or greater than the threshold reliability on the basis of the currently available digital biomarker data, the digital biomarker type data 1410 may include information regarding a digital biomarker (first type) which is additionally necessary for increasing the reliability of diagnostic result data, as well as the currently available biomarker. When the additionally necessary digital biomarker (first type) cannot be obtained on the basis of a digital biomarker module, a user may request the diagnosis server to provide a digital biomarker (second type) obtained through a question transmitted to the user through the user equipment. The digital biomarker (second type) may replace the additionally necessary digital biomarker (first type) to increase reliability. The reliability of diagnostic result data may be improved through the digital biomarker (second type).

For example, when it is difficult to obtain digital biomarker data regarding a digital biomarker (tension, first type) due to the absence of a smart belt with a Hall sensor, the diagnosis server may ask a user a question for obtaining digital biomarker data (tension) through user equipment and obtain digital biomarker data (tension, second type) through the user equipment on the basis of user input data.

A method of determining the digital biomarker operation data 1420 as digital biomarker control data by the diagnosis server will be described below. The diagnosis server may determine an operation cycle of the digital biomarker module for obtaining digital biomarker data, an operation time of the digital biomarker module, the amount of data to be obtained by the digital biomarker module, etc. on the basis of previously obtained digital biomarker data and prescription data.

For example, a time when digital biomarker data is to be obtained by the digital biomarker module may vary according to the type of prescription data. For example, digital biomarker data for obtaining sleep environment information related to insomnia may be obtained at a time when a user falls asleep or a time during which the user is sleeping, and digital biomarker data related to obesity may be obtained at a time during which the user is eating food.

The amount of data to be obtained by the digital biomarker module and the like may be determined on the basis of the severity of a disease included in the prescription data and a time when next diagnostic result data is to be generated. For example, the digital biomarker motion data 1420 may be set such that the more severe the disease is, the shorter a time until next diagnostic result data is generated and the more the amount of data is to be obtained by the digital biomarker module.

In addition, the diagnosis server may determine the digital biomarker operation data 1420 on the basis of digital biomarker data that has been obtained by the user equipment. The digital biomarker operation data 1420 may be determined by taking into account an operation cycle of the digital biomarker module, an operation time of the digital biomarker module, the amount of data to be obtained by the digital biomarker module, and the like to improve data with low reliability among the obtained digital biomarker data.

According to the digital biomarker operation data 1420, an ON/OFF pattern of the digital biomarker module, a sleep mode/active mode period, etc. may be determined and digital biomarker data may be collected without unnecessary power consumption of the user equipment.

In addition, the diagnosis server may determine the digital biomarker collection completion condition data 1430.

The digital biomarker collection completion condition data 1430 may be set in consideration of digital biomarker data necessary to generate next diagnostic result data (next prescription data). The reliability of digital biomarker data to be obtained for each of a plurality of digital biomarkers, a section in which digital biomarker data is to be obtained, and the like may be set according to the type of a disease, user characteristics (gender, age, height, weight, etc. of a user), and a medical treatment schedule. The reliability of the digital biomarker data to be obtained and the section in which the digital biomarker data is to be obtained may be set as the digital biomarker collection completion condition data 1430.

Figure 15:
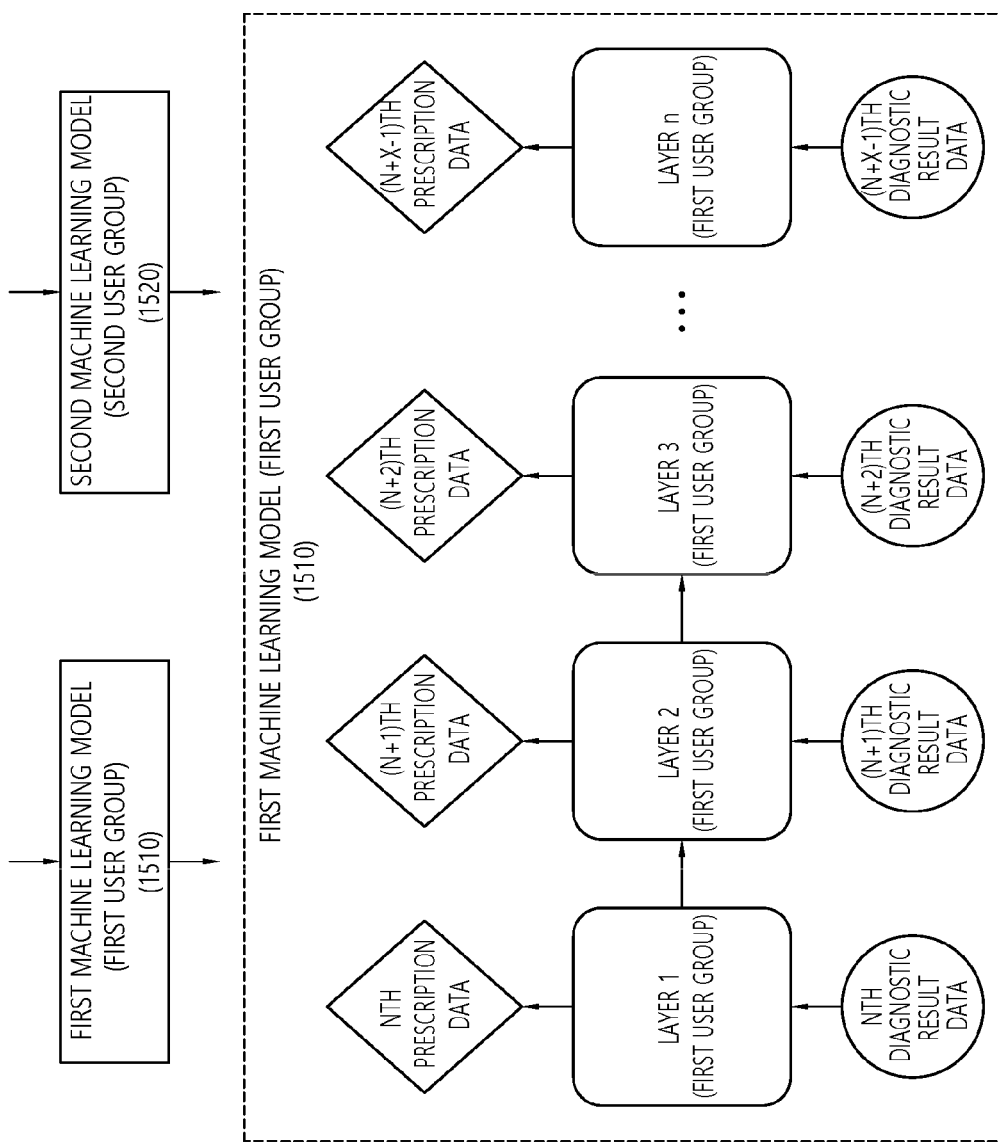
FIG. 15 is a conceptual diagram of a method of performing learning on the basis of prescription data and diagnostic result data according to an embodiment of the present disclosure.

FIG. 15 is a conceptual diagram of a method of performing learning on the basis of prescription data and diagnostic result data according to an embodiment of the present disclosure.

FIG. 15 illustrates a method of increasing the accuracy of diagnostic result data and prescription data through machine learning.

Referring to FIG. 15, prescription data and diagnostic result data may be input to a machine learning engine, and the machine learning engine may be trained with a change in a user's condition according to a prescription on the basis of the prescription data and the diagnostic result data and thus may predict an effect of the prescription and provide more optimal prescription data to the user.

Such a machine learning engine may be created differently according to a certain disease and the user's characteristics (severity of the disease, the user's gender, age, height, weight, and health status, etc.), and differently created machine learning engines may be integrated in consideration of results of training of the machine learning engine. This will be described in detail below.

For example, it is assumed that there are prescription data and diagnostic result data that have been effective in treating alcoholism and learning is performed by dividing user groups into two user groups (first user group and second user group) according to users' characteristics. For example, user groups may be classified according to gender.

A method of generating a first machine learning model (first user group) 1510 and a second machine learning model (second user group) 1520 is provided.

The first machine learning model (first user group) 1510 may be modeled based on training data (prescription data and diagnostic result data) of the first user group.

The second machine learning model (second user group) 1520 may be modeled based on training data (prescription data and diagnostic result data) of the second user group. Diagnostic result data and prescription data that are input to the first machine learning model (first user group) 1510 and the second machine learning model (second user group) 1520 may be pre-processed diagnostic result data and prescription data each having an effect equal to or greater than a threshold level.

The first machine learning model (first user group) 1510 and the second machine learning model (second user group) 1520 are implemented on the basis of a plurality of layers as will be described below and may be implemented to identify a change over time and a status of a user, e.g., caused when diagnostic result data and prescription data are generated.

Diagnostic result data generated for an $n^{th}$ time may be referred to as $n^{th}$ diagnostic result data, and prescription data according to the $n^{th}$ diagnostic result data may be $n^{th}$ prescription data.

Second diagnostic result data obtained after a prescription according to the $n^{th}$ prescription data may be referred to as $(n+1)^{th}$ diagnostic result data, and prescription data according to the $(n+1)^{th}$ diagnostic result data may be $(n+1)^{th}$ prescription data.

In this way, $(n+a)^{th}$ diagnostic result data and $(n+a)^{th}$ prescription data obtained over time with respect to a certain disease of a user may be learned by inputting them to the first machine learning model 1510 and the second machine learning model 1520.

Although for convenience of description, only a method of learning the first machine learning model 1510 corresponding to the first user group will be described herein, this method may apply to learning of the second machine learning model 1520 corresponding to the second user group.

The first machine learning model (first user group) 1510 may include a first layer (first user group), a second layer (first user group), a third layer (first user group), . . . , an $x^{th}$ layer (first user group).

(1) $n^{th}$ diagnostic result data and $n^{th}$ prescription data may be respectively input as an input value and an output value to the first layer (first user group) of the first machine learning model (first user group) 1510.

(2) $(n+1)^{th}$ diagnostic result data and $(n+1)^{th}$ prescription data may be respectively input as an input value and an output value to the second layer (first user group) of the first machine learning model (first user group) 1510.

(3) $(n+2)^{th}$ diagnostic result data and $(n+2)^{th}$ prescription data may be respectively input as an input value and an output value to the third layer (first user group) of the first machine learning model (first user group) 1510.

In this way, $(n+x-1)^{th}$ diagnostic result data and $(n+x-1)^{th}$ prescription data may be respectively input as an input value and an output value to the $x^{th}$ layer (first user group) of the first machine learning model (first user group) 1510.

The number of all layers of a machine learning model may be adaptively set to an optimal value for determining an effect of diagnostic data or may be set in consideration of characteristics of a certain disease, characteristics of training data, and characteristics of a user group. For example, the number of layers of the machine learning model may be relatively large when long-term treatment for a certain disease is required, and may be relatively small when long-term treatment for the certain disease is not required.

When the layers of the machine learning model are learned in this manner, more optimal prescription data may be provided by adaptively reflecting characteristics of a user and a disease when diagnostic result data is input.

Figure 16:
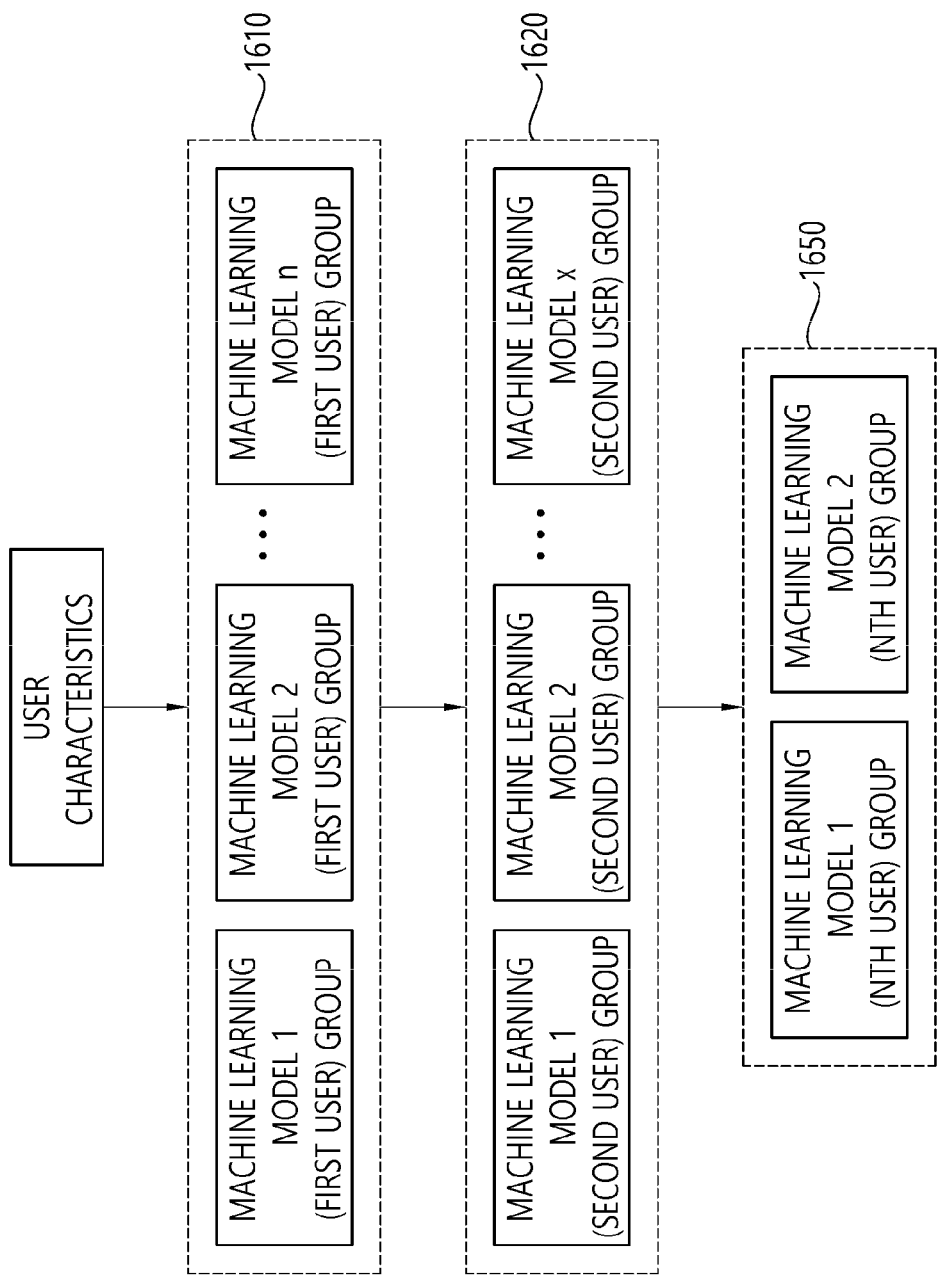
FIG. 16 is a conceptual diagram of a method of performing learning on the basis of prescription data and diagnostic result data according to another embodiment of the present disclosure.

FIG. 16 is a conceptual diagram of a method of performing learning on the basis of prescription data and diagnostic result data according to another embodiment of the present disclosure.

FIG. 16 illustrates a method of using a machine learning model on the basis of feedback on prescription data.

Referring to FIG. 16, a machine learning model for a certain disease may be generated differently according to a user's characteristics (severity of the disease, the users' gender, age, height, weight, and health status, etc.).

A plurality of machine learning models may be created by setting a relatively large number of first user groups by reflecting differences in user characteristics for grouping according to user characteristics as much as possible.

Thereafter, after a plurality of machine learning models (first user group) 1610 for the first user group are generated, the difference between output values from the plurality of machine learning models with respect to the same diagnostic result data may be identified. After the number of pieces of diagnostic result data, which is equal to or greater than a threshold number, is input, machine learning models outputting the same output value may be integrated into one machine learning model, and user groups before the integration may be integrated into one user group and training data of the resultant user group may be input to re-generate a machine learning model. After the plurality of machine learning models (first user group) 1610 are generated, user groups may be integrated to generate at least one machine learning model (second user group) 1620.

In this way, when a machine learning model ($n^{th}$ user group) 1650 having no difference in prescription data is generated, the machine learning model 1650 may be used to generate prescription data.

Through this method, more reinforced learning may be performed by optimizing a machine learning model in consideration of characteristics of a disease and a user.

According to the present disclosure, a user's health condition can be effectively diagnosed by obtaining digital biomarker data.

According to the present disclosure, prescription data can be generated on the basis of digital biomarker data, and user health management can be effectively performed by a user through user equipment according to the prescription data.

According to the present disclosure, the operation of a digital biomarker module of a user equipment can be controlled according to diagnostic result data and prescription data.

In addition, according to the present disclosure, optimal prescription data can be provided according to diagnostic result data through machine-learning-based learning on the basis of a user's diagnostic result data and prescription data.

The embodiments according to the present disclosure described above may be implemented in the form of program instructions executable through various computer components and recorded on a computer-readable recording medium. The computer-readable recording medium may store program instructions, data files, data structures, and the like solely or in combination. The program instructions recorded on the computer-readable recording medium may be specially designed and configured for the present disclosure or may be known to and usable by those of ordinary skill in the computer software field. Examples of the computer-readable recording medium include magnetic media such as hard disks, floppy disks and magnetic tapes, optical recording media such as CD-ROMs and DVDs, magneto-optical media such as floptical disks, and hardware devices, such as ROM, RAM, and flash memory, which are specially configured to store and execute program instructions. Examples of the program instructions include not only machine code generated by a compiler but also high-level language code executable by a computer using an interpreter or the like. The hardware devices may be changed to one or more software modules to perform processing according to the present disclosure and vice versa.

Although the present disclosure has been described above with respect to specific matters such as specific components and limited embodiments and drawings, these embodiments are provided only to help a more general understanding of the present disclosure and the present disclosure is not limited thereto, and various modifications and changes may be made therein by those of ordinary skill in the art on the basis of the above description.

Therefore, the spirit of the present disclosure is limited to the above-described embodiments, and it should be understood that all ranges that are equivalent to or equivalently changed from the following claims as well as the following claims are within the scope of the spirit of the present disclosure.

What is claimed is:

1. A method of controlling user equipment for providing a diagnosis for a target condition, the user equipment being a phone, a watch, a belt, or other device worn or possessed by a user and including a sensor therein or thereon, the method comprising:

receiving, by a diagnosis server, prescription data from a prescription server, the prescription data being generated on the basis of diagnostic result data input to a machine learning engine;

generating, by the diagnosis server, digital biomarker control data on the basis of the prescription data, wherein the digital biomarker control data comprises digital biomarker type data that include information for controlling the sensor of the user equipment, the digital biomarker control data further comprising at least one of digital biomarker operation data and digital biomarker collection completion condition data;

determining, by the diagnosis server, whether diagnostic result data with reliability equal to or greater than a threshold reliability is obtainable by the user equipment on the basis of currently available digital biomarker data, wherein the digital biomarker type data includes information regarding a digital biomarker for increasing the reliability of diagnostic result data when it is difficult to obtain diagnostic result data with reliability equal to or greater than the threshold reliability;

transmitting, by the diagnosis server, the digital biomarker control data to the user equipment to control at least one of an operation cycle, an operation period, and an amount of data collected by the sensor, wherein the digital biomarker control data comprises information that controls the sensor of the user equipment to collect digital biomarker data according to the prescription data, the sensor measuring at least one of acceleration, heart rate, electrodermal activity, and tension of the user based on the digital biomarker control data;

receiving, by the diagnosis server, the digital biomarker data collected according to the prescription data;

inputting, by the diagnosis server, the prescription data and the diagnostic result data into the machine learning engine, the engine dividing users into two or more groups according to user characteristics including gender, age, height or weight, wherein in a first layer within each group diagnostic result data generated for an $n^{th}$ time is categorized as $n^{th}$ diagnostic result data and inputted as an input value to the first layer and prescription data according to the $n^{th}$ diagnostic result data is categorized as $n^{th}$ prescription data and inputted as an output value to the first layer, wherein in a second layer within each group diagnostic result data obtained after a prescription according to the $n^{th}$ prescription data is categorized to as $(n+1)^{th}$ diagnostic result data and inputted as an input value to the second layer and prescription data according to the $(n+1)^{th}$ diagnostic result data is categorized as $(n+1)^{th}$ prescription data and inputted to as an output value to the second layer, wherein in an $n^{th}$ layer within each group $(n+a)^{th}$ diagnostic result data and $(n+a)^{th}$ prescription data obtained over time with respect to a certain condition of a user is learned; and transmitting, by the diagnosis server, a diagnosis of a target condition generated by the machine learning engine to the phone of the user.

2. The method of claim 1, wherein the target condition is selected from the group consisting of drug addiction, alcoholism, insomnia, sarcopenia, epilepsy, and obesity.

3. The method of claim 1, wherein the currently available digital biomarker data is obtainable through the sensor of the user equipment and answers received from the user through the user equipment based on questions asked of the user through the user equipment.

4. The method of claim 1, wherein the prescription data is i) data for administering medicine to treat the target condition, ii) data for correcting a behavior of the user to treat the target condition, or iii) data for recommended exercise to treat the target condition.

5. The method of claim 1, wherein the digital biomarker control data is changed according to the number of times the prescription data is received by the diagnosis server.

6. The method of claim 1, wherein the amount of data is determined considering the severity of a disease included in the prescription data, and wherein the operation period is determined based on the type of disease included in the prescription data.

7. The method of claim 6, wherein a total number of layers in each group of the machine learning engine is adaptively set considering characteristics of a specific disease, characteristics of training data, or characteristics of user groups.

8. A diagnosis server for controlling user equipment for providing a diagnosis for a target condition, the user equipment being a phone, a watch, a belt, or other device worn or possessed by a user and including a sensor therein or thereon, the server comprising:
  a communicator configured to communicate with user equipment; and
  a processor operatively connected to the communicator, wherein the processor is configured to:
    receive prescription data, the prescription data being generated on the basis of diagnostic result data input to a machine learning engine;
    generate digital biomarker control data on the basis of the prescription data, wherein the digital biomarker control data comprises digital biomarker type data that includes information for controlling the sensor of the user equipment, the digital biomarker control data further comprising at least one of digital biomarker operation data and digital biomarker collection completion condition data;
    determine whether diagnostic result data with reliability equal to or greater than a threshold reliability is obtainable by user equipment on the basis of currently available digital biomarker data, wherein the digital biomarker type data includes information regarding a digital biomarker for increasing the reliability of diagnostic result data when it is difficult to obtain diagnostic result data with reliability equal to or greater than the threshold reliability;
    transmit the digital biomarker control data to the user equipment to control at least one of an operation cycle, an operation period, and an amount of data collected by the user, wherein the digital biomarker control data comprises information that controls the sensor of the user equipment to collect digital biomarker data according to the prescription data, the sensor measuring at least one of acceleration, heart rate, electrodermal activity, and tension of the user based on the digital biomarker control data;
    receive the collected digital biomarker data;
    input the prescription data and the diagnostic result data into the machine learning engine, the engine dividing users into two or more groups according to user characteristics including gender, age, height or weight, wherein in a first layer within each group diagnostic result data generated for an $n^{th}$ time is categorized as $n^{th}$ diagnostic result data and inputted as an input value to the first layer and prescription data according to the $n^{th}$ diagnostic result data is categorized as $n^{th}$ prescription data and inputted as an output value to the first layer, wherein in a second layer within each group diagnostic result data obtained after a prescription according to the $n^{th}$ prescription data is categorized to as $(n+1)^{th}$ diagnostic result data and inputted as an input value to the second layer and prescription data according to the $(n+1)^{th}$ diagnostic result data is categorized as $(n+1)^{th}$ prescription data and inputted as an output value to the second layer, wherein in an $n^{th}$ layer within each group $(n+a)^{th}$ diagnostic result data and $(n+a)^{th}$ prescription data obtained over time with respect to a certain condition of a user is learned; and
    transmit a diagnosis of a target condition generated by the machine learning engine to the phone of the user.

9. The diagnosis server of claim 8, wherein the target condition is selected from the group consisting of drug addiction, alcoholism, insomnia, sarcopenia, epilepsy, and obesity.

10. The diagnosis server of claim 8, wherein the currently available digital biomarker data is obtainable through the sensor of the user equipment and answers received from the user through the user equipment based on questions asked of the user through the user equipment.

11. The diagnosis server of claim 8, wherein the prescription data is i) data for administering medicine to treat the target condition, ii) data for correcting a behavior of the user to treat the target condition, or iii) data for recommended exercise to treat the target condition.

12. The diagnosis server of claim 8, wherein the digital biomarker control data is changed according to the number of times the prescription data is received by the diagnosis server.

13. The diagnosis server of claim 8, wherein the amount of data is determined considering the severity of a disease included in the prescription data, and wherein the operation period is determined based on the type of disease included in the prescription data.

14. The diagnosis server of claim 8, wherein a total number of layers in each group of the machine learning engine is adaptively set considering characteristics of a specific disease, characteristics of training data, or characteristics of user groups.

* * * * *